(12) United States Patent
Baschong et al.

(10) Patent No.: US 10,098,849 B2
(45) Date of Patent: Oct. 16, 2018

(54) ANTI-RADICAL AGENTS

(75) Inventors: Werner Baschong, Basel (CH); Oliver Reich, Grenzach-Wyhlen (DE); Sébastien Mongiat, Sierentz (FR)

(73) Assignee: BASF SE, Ludwigshafen (DE)

( * ) Notice: Subject to any disclaimer, the term of this patent is extended or adjusted under 35 U.S.C. 154(b) by 603 days.

(21) Appl. No.: 13/603,807

(22) Filed: Sep. 5, 2012

(65) Prior Publication Data

US 2012/0328541 A1    Dec. 27, 2012

Related U.S. Application Data

(62) Division of application No. 11/792,745, filed as application No. PCT/EP2005/055475 on Oct. 24, 2005.

(30) Foreign Application Priority Data

Dec. 22, 2004  (EP) .................................... 04106821

(51) Int. Cl.
*A61K 31/075*  (2006.01)
*C07C 43/20*  (2006.01)
(Continued)

(52) U.S. Cl.
CPC ............ *A61K 31/05* (2013.01); *A61K 8/11* (2013.01); *A61K 8/14* (2013.01); *A61K 8/347* (2013.01); *A61K 8/37* (2013.01); *A61K 8/375* (2013.01); *A61K 8/42* (2013.01); *A61K 8/46* (2013.01); *A61K 8/466* (2013.01); *A61K 8/498* (2013.01); *A61K 8/4926* (2013.01);
(Continued)

(58) Field of Classification Search
USPC ............................................. 424/59; 514/721
See application file for complete search history.

(56) References Cited

U.S. PATENT DOCUMENTS

| 3,112,338 A | 11/1963 | Smutny et al. ............... 260/473 |
| 4,857,572 A | 8/1989 | Meier et al. .................. 524/289 |

(Continued)

FOREIGN PATENT DOCUMENTS

| EP | 1 366 763 | 12/2003 |
| WO | 92/22290 | 12/1992 |

(Continued)

OTHER PUBLICATIONS

Brtko et al. (Cent. Eur. J. Publ. Health. 12 Suppl. p. S16-S18 (2004).*

(Continued)

Primary Examiner — Anna R Falkowitz
(74) Attorney, Agent, or Firm — Marshall, Gerstein & Borun LLP

(57) ABSTRACT

Compounds of the formulae and selected hindered nitroxyl, hydroxylamine and hydroxylamine salt compounds such as the compound of the formula wherein $G_1$ is hydrogen; $C_1$-$C_{22}$alkyl; $C_1$-$C_{22}$alkylthio; $C_2$-$C_{22}$alkylthioalkyl; $C_5$-$C_7$cycloalkyl; phenyl; $C_7$-$C_9$-phenylalkyl; or $SO_3M$; $G_2$ is $C_1$-$C_{22}$alkyl; $C_5$-$C_7$cycloalkyl; phenyl; or $C_7$-$C_9$-phenylalkyl; E is oxyl or hydroxyl; V is —O—; or —NH—; a is 0 or 1 or 2; b, c and d and g are each independently of one another 0 or 1;

e is an integer from 1 to 4;

f, m, n and p are each independently of one another an integer from 1 to 3;

q is 0 or an integer from 1 to 3;

Q, T and $G_3$ are as defined in claim 1;

$G_4$ and $G_5$ are each independently of the other hydrogen; or $C_1$-$C_{22}$alkyl;

exhibit marked antiinflammatory action.

9 Claims, No Drawings

(51) Int. Cl.

| | |
|---|---|
| A61K 31/05 | (2006.01) |
| A61K 8/11 | (2006.01) |
| A61K 8/14 | (2006.01) |
| A61K 8/34 | (2006.01) |
| A61K 8/37 | (2006.01) |
| A61K 8/42 | (2006.01) |
| A61K 8/46 | (2006.01) |
| A61K 8/49 | (2006.01) |
| A61K 8/55 | (2006.01) |
| A61K 8/67 | (2006.01) |
| A61K 31/165 | (2006.01) |
| A61K 31/222 | (2006.01) |
| A61K 31/255 | (2006.01) |
| A61K 31/34 | (2006.01) |
| A61K 31/445 | (2006.01) |
| A61Q 17/04 | (2006.01) |
| A61Q 19/00 | (2006.01) |
| A61Q 1/02 | (2006.01) |
| A61Q 5/02 | (2006.01) |
| A61Q 11/00 | (2006.01) |
| A61Q 19/10 | (2006.01) |

(52) U.S. Cl.
CPC .......... *A61K 8/4966* (2013.01); *A61K 8/4973* (2013.01); *A61K 8/553* (2013.01); *A61K 8/671* (2013.01); *A61K 8/676* (2013.01); *A61K 31/165* (2013.01); *A61K 31/222* (2013.01); *A61K 31/255* (2013.01); *A61K 31/34* (2013.01); *A61K 31/445* (2013.01); *A61Q 17/04* (2013.01); *A61Q 19/00* (2013.01); *A61K 2800/412* (2013.01); *A61K 2800/413* (2013.01); *A61K 2800/522* (2013.01); *A61Q 1/02* (2013.01); *A61Q 5/02* (2013.01); *A61Q 11/00* (2013.01); *A61Q 19/10* (2013.01)

(56) References Cited

U.S. PATENT DOCUMENTS

| | | | |
|---|---|---|---|
| 6,337,320 B1 * | 1/2002 | Hersh et al. | 514/9.4 |
| 6,403,627 B1 | 6/2002 | Carney et al. | 514/400 |
| 7,056,742 B2 * | 6/2006 | Meyer et al. | 435/468 |
| 2003/0069453 A1 * | 4/2003 | Fankhauser et al. | 568/819 |
| 2004/0024025 A1 | 2/2004 | Kasid et al. | 514/326 |
| 2004/0102446 A1 * | 5/2004 | Pflucker et al. | 514/250 |

FOREIGN PATENT DOCUMENTS

| | | | | |
|---|---|---|---|---|
| WO | 96/40127 | | 12/1996 | |
| WO | WO02/072583 | * | 2/2002 | C07D 487/04 |
| WO | 03/024417 | | 3/2003 | |
| WO | WO03/024417 | * | 5/2003 | A61K 7/48 |
| WO | 2005/000829 | | 1/2005 | |

OTHER PUBLICATIONS

FDA (Cosmetic Guidance, Compliance & Regulatory Information www.fda.gov/Cosmetics/GuidanceComplianceRegulatoryInformation/ucm074201.htm 2012).*
Merriam-Webster (Dictionary/Thesaurus, 2012).*
Brtko et al., Kojic Acid and its Derivatives: History and Present State of the Art: Cent. Eur. J. Publ. Health. 12, Supp. p. S16-S18 (2004).
Simeng Suy et al., The Journal of Biological Chemistry, vol. 273, No. 28, pp. 17871-17878, (Jul. 1998).
H.G.S. Rathore et al., Journal of the Indian Chemical Society, vol. 61, pp. 556-558, (Jun. 1984).
G. Roy et al., The Journal of Membrane Biology, vol. 162, pp. 191-200 (1998).
Simeng Suy et al., Cancer, vol. 103, No. 6, pp. 1302-1313 (Mar. 2005).

* cited by examiner

ANTI-RADICAL AGENTS

This application is a divisional of co-pending application Ser. No. 11/792,745 filed on Mar. 18, 2008 which is the National Stage of International Application PCT/EP2005/055475, filed Oct. 24, 2005, the contents of which are herein incorporated by reference.

The present invention relates to the use especially of carbon or ester/amide bridged phenols or lactones thereof, or some sterically hindered amines, as pharmaceutically active agents and to pharmaceutical, especially dermatological, compositions containing them. The invention further relates to the use of these compounds for the preparation of medicaments or formulations for the treatment of radical induced impairments such as inflammatory or allergic conditions, collagen damages, DNA-damage, or reperfusion-damage (use as anti aging).

It is standard practice to use glucocorticoids for the topical treatment of inflammatory and allergic conditions. It is common knowledge that these compounds can have unwanted side-effects.

Owing to their insufficient ability to penetrate the skin, nonsteroidal antiinflammatory medicaments containing therapeutic agents such as ketoprofen, BW755c, piroxicam, diclofenac or indomethazin cannot effectively be applied topically, but only systemically. Also some phenol ethers have been proposed having antioxidant, anti-inflammatory and antiallergic properties (see EP-A-1366763 and literature cited therein).

It is the object of this invention to provide pharmaceutical compositions having surprisingly good pharmacologically properties, in particular antioxidant, anti-inflammatory and antiallergic properties, especially when administered locally.

It has been found that compounds of the formulae

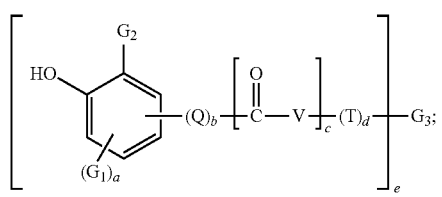

(1)

and/or

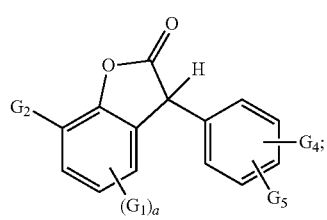

(2)

and/or (3) hindered nitroxyl compounds, hindered hydroxylamine compounds, hindered hydroxylamine salt compounds of the formulae

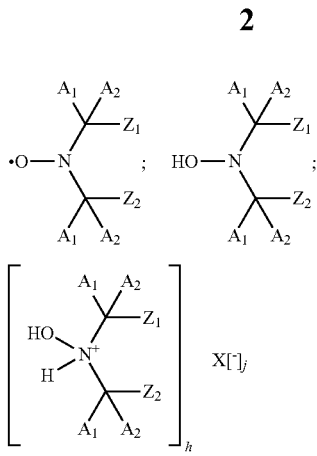

where in the above formulae $G_1$ is hydrogen; $C_1$-$C_{22}$alkyl; $C_1$-$C_{22}$alkylthio; $C_2$-$C_{22}$alkylthioalkyl; $C_5$-$C_7$cycloalkyl; phenyl; $C_7$-$C_9$-phenylalkyl; or $SO_3M$;

$G_2$ is $C_1$-$C_{22}$alkyl; $C_5$-$C_7$cycloalkyl; phenyl; or $C_7$-$C_9$-phenylalkyl;

Q is —$C_mH_{2m}$—;

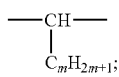

$C_mH_{2m+1}$;

—$C_mH_{2m}$—NH; a radical of formula

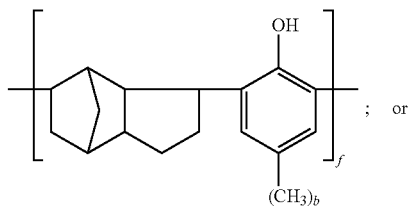

(1a)

(1b)

T is —$C_nH_{2n}$—; —$(CH_2)_n$—O—$CH_2$—; phenylene;

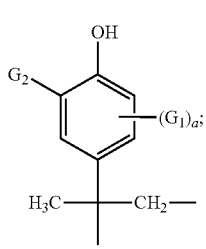

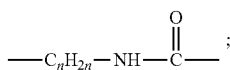

or a radical of formula

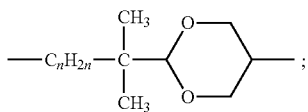  (1c)

V is —O—; or —NH—;

a is 0; 1; or 2;

b, c and d and g are each independently of one another 0; or 1;

e is an integer from 1 to 4;

f is an integer from 1 to 3; and m, n and p are each independently of one another an integer from 1 to 3;

q is 0 or an integer from 1 to 3;

if e=1, or in formula (3), then $G_3$ is hydrogen; $C_1$-$C_{22}$alkyl; $C_5$-$C_7$cycloalkyl; $C_1$-$C_{22}$alkylthio; $C_2$-$C_{22}$alkylthioalkyl; $C_2$-$C_{18}$alkenyl; $C_1$-$C_{18}$phenylalkyl; M; $SO_3$M; a radical of formula

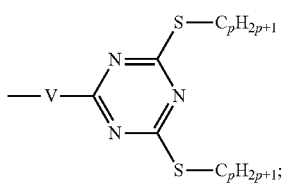  (1d)

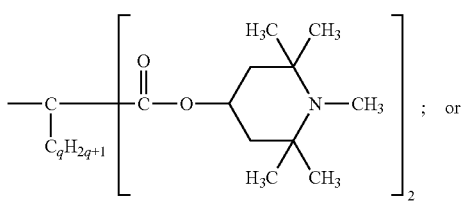  (1e)

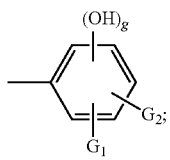  (1f)

or $G_3$ is propyl substituted by OH and/or by $C_2$-$C_{22}$alkanoyloxy;

M is alkali; ammonium; H;

if e=2, then $G_3$ is a direct bond; —$CH_2$—;

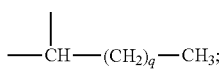

or —S—; or $G_3$ is propyl substituted by OH or $C_2$-$C_{22}$alkanoyloxy;

if
e=3, then
$G_3$ is the radical of formula

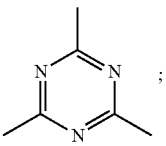  (1g)

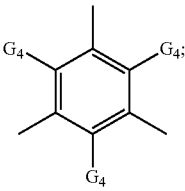  (1h)

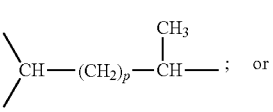  (1i)

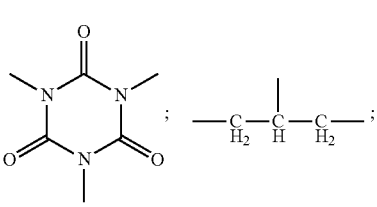  (1k)

if
e=4, then
$G_3$ is

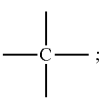  ;

$G_4$ and $G_5$ are each independently of the other hydrogen; or $C_1$-$C_{22}$alkyl;

$A_1$ and $A_2$ are independently alkyl of 1 to 4 carbon atoms or are together pentamethylene, $Z_1$ and $Z_2$ are each methyl, or $Z_1$ and $Z_2$ together form a linking moiety which may additionally be substituted by an ester, ether, hydroxy, oxo, cyanohydrin, amide, amino, carboxy or urethane group, h is the number of positive charges and j is the number of negative charges, X is an inorganic or organic anion, and where the total charge of cations h is equal to the total charge of anions j, exhibit marked radical scavenging and antiinflammatory action in cellular and enzymatic in vitro assays and in in vivo assays on human volunteers, while showing good skin and cell compatibility. Present compounds can be used alone or as mixtures with each other and/or further components, e.g. those described further below. Present invention therefore pertains to a pharmaceutical composition comprising at least one compound of formulae (1), (2) and/or (3), together with a pharmaceutically acceptable carrier or adjuvant, as well as to the use of a compound of formulae (1), (2) and/or (3) for the preparation of a medicament or a formulation, such as a cosmetic or pharmaceutic formulation, for the treatment or prevention of radical-induced skin damage and inflammatory and allergic conditions.

Compounds of the formula 1, where e is 1, usually contain the spacer groups Q and (CO)—V, which corresponds to the condition b=c=1. Also useful are the compounds of formulae (16)

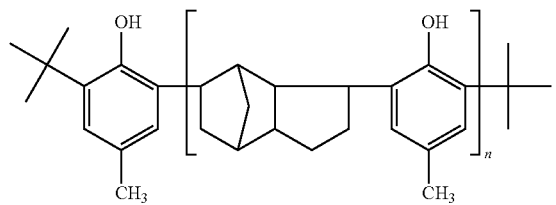

n = 1 - 3

(18)

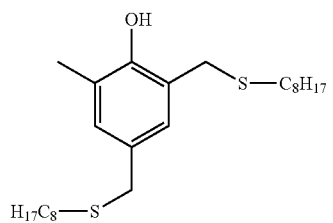

(20)

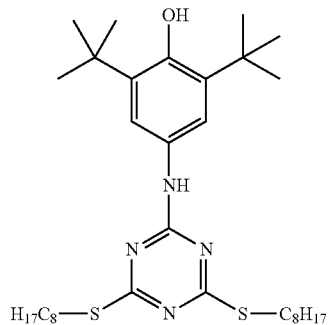

(21)

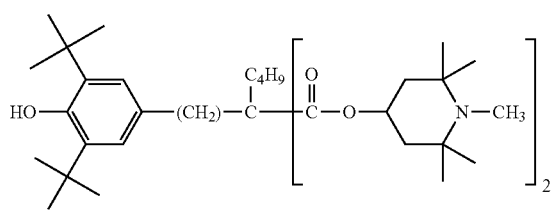

(22)

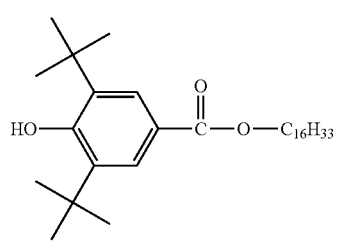

(23)

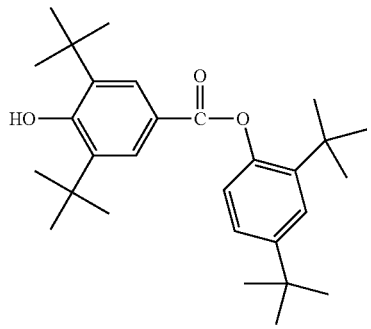

Radical Oxygen Species (ROS) are known to oxidize lipids, break down enzymes and matrix proteins, affect the DNA or the RNA and are leading to the premature ageing of the skin with drying effect, loss of elasticity, strong irritation and promoting the destruction of constituents inside skin. Inflammation and ROS generation activate the matrix metalloproteinases (MMP) but also cause oxidative damage to cellular proteins, lipids and carbohydrates.

MMPs are a group of Zinc-dependent endopeptidases capable of degrading Extra Cellular Matrix (ECM) components such as collagen, elastin, fibronectin, gelatine, laminin, leading to photo-aged skin with wrinkle lines and dispigmentation reactions. The present compounds are able to enhance the endogeneous antioxidant defense system which includes enzymatic components such as Glutathione peroxidase, Catalase, Superoxide dismutase, Methallothionein; or non enzymatic components such as Glutathione, vitamin E, Vitamin C, Ubiquinol, β-carotene.

After the application to the skin, the compounds can protect intercellular and intracellular lipids, lipoproteins, cell membranes, low molecular compounds, such as lipids, sugars, labile amino acids (e.g. with thiol group), glutathione, and further macromolecules such as proteins, proteoglycanes and glycosaminoglycanes against direct oxidation.

An additional effect from those substances is their protective effect upon the components of the preparation in question that are sensitive to oxidation by air oxygen, which offers the benefit of higher stability of the product and its longer shelf life. A part of pharmaceutical or cosmetic carrier emulsions are lipids and also emulsifiers containing lipid segments, which makes them easily prone to chemical conversions induced by reaction with oxygen.

According to the chemical structure and solubility in various phases of typical pharmaceutical or cosmetic carriers, the compounds may be hydrophilic or lipophilic. The choice of an optimum antioxidant does not depend just on the solubility in a certain carrier system, but it is also affected by undesirable interactions with a carrier, skin penetration ability after a topical application of the preparation, possibly the production of cytotoxic or immunosuppressive products of a reaction with free radicals, with or without combined action of UV light.

Damage of radicals in the organism of animals and humans, which may be prevented by the present compounds, has been described in further detail in U.S. Pat. No. 4,698,360.

The present compounds, e.g. those of formulae (1), (2) and/or (3), are useful for the treatment of inflammatory and allergic conditions (e.g. as described by Skaper et al., Free Radical Biology and Medicine 22, 669-78 (1997)), as well as for the treatment of conditions involving disturbances of cell proliferation. They are preferably used for the local treatment of radical-induced adverse reactions such as inflammatory and allergic conditions collagen damage, reperfusion damage, DNA-damage; especially for the skin treatment.

In vitro assays show that the present compounds inhibit the formation of different mediators that are an important factor in inflammation.

The present compounds take effect as radical inhibitor. They represent lipoxygenase/-cyclooxigenase inhibitors, i.e. they can intervene in the inflammatory cascade. It can be shown that they take effect as anti-inflammatory agent for the UV induced erythema. They show anti-inflammatory and antioxidant effect, which in certain applications is comparable to the one of vitamin E.

The hindered nitroxyl, hydroxylamine and hydroxylamine salt compounds (3) are for example of formulae A to EE and A* to EE*

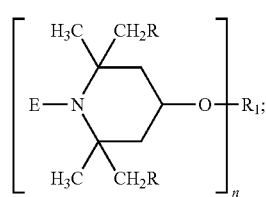
(A)

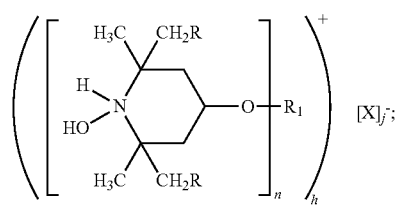
(A*)

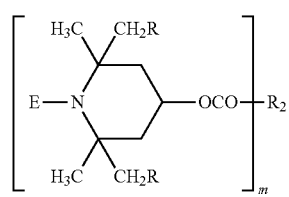
(B)

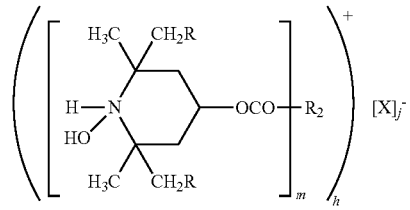
(B*)

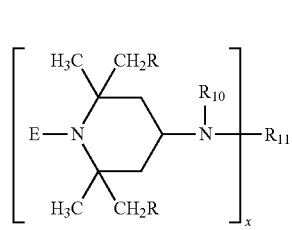
(C)

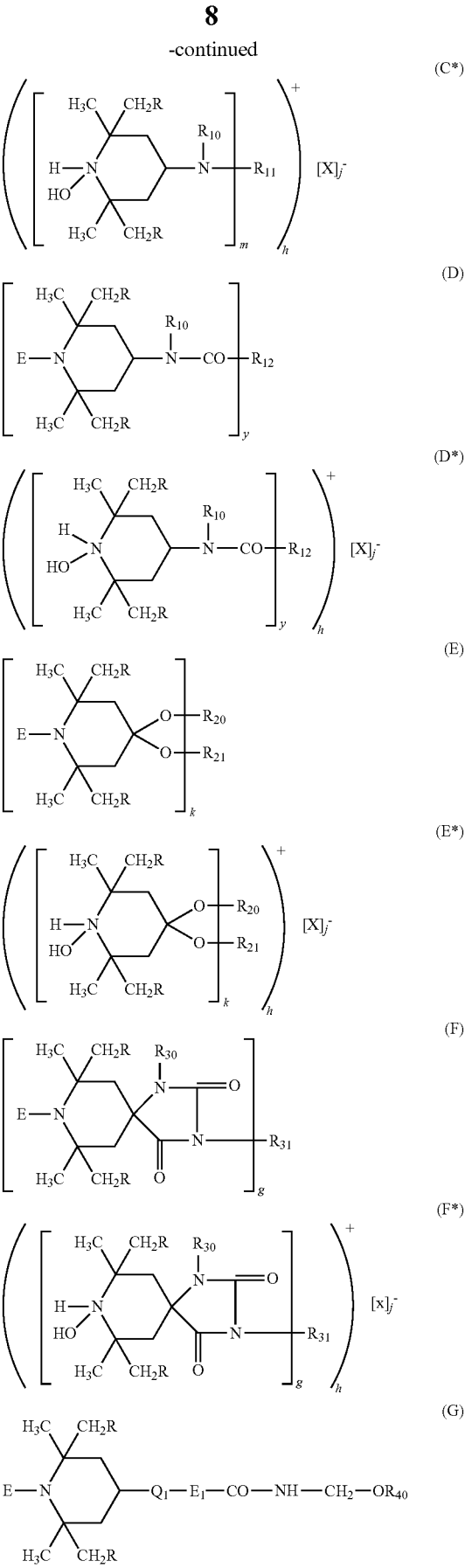

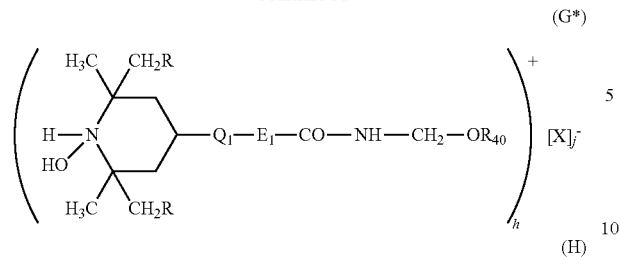
(G*)
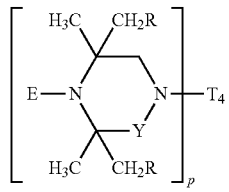
(H)
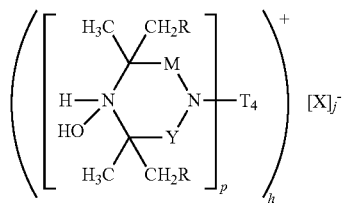
(H*)
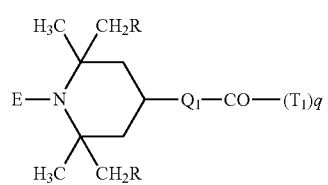
(I)
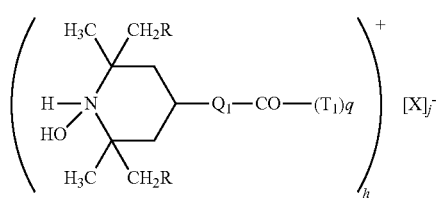
(I*)
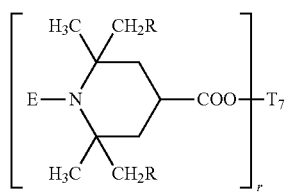
(J)
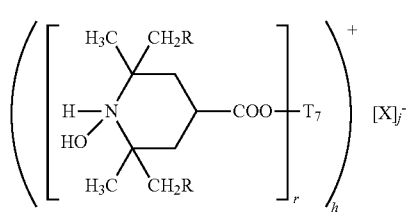
(J*)
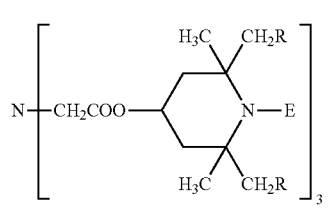
(K)
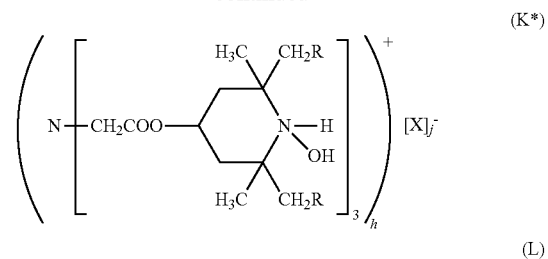
(K*)
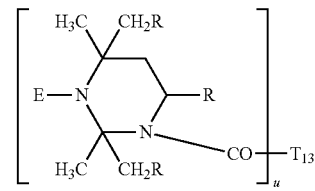
(L)
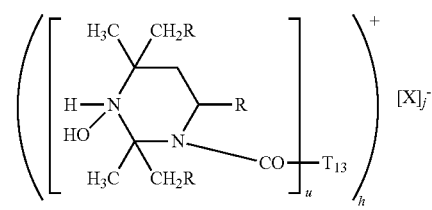
(L*)
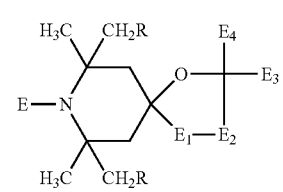
(M)
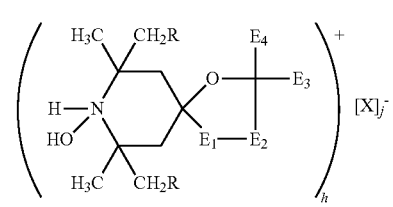
(M*)
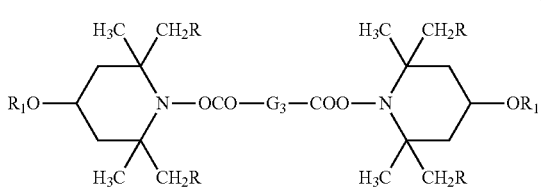
(N)
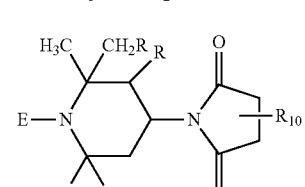
(O)
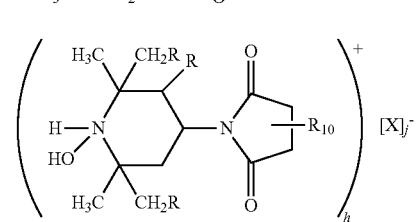
(O*)

11
-continued
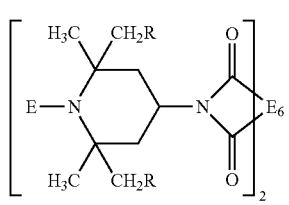
(P)
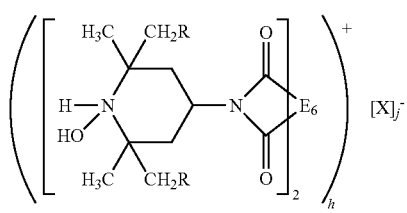
(P*)
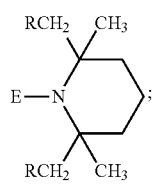
(Q)
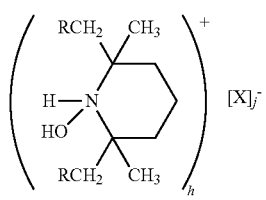
(Q*)
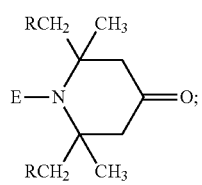
(R)
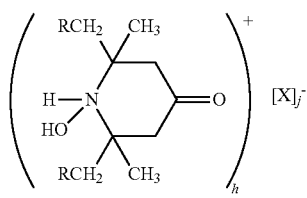
(R*)
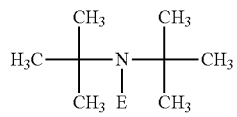
(S)
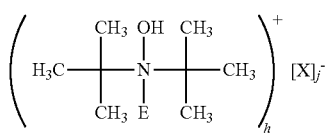
(S*)
12
-continued
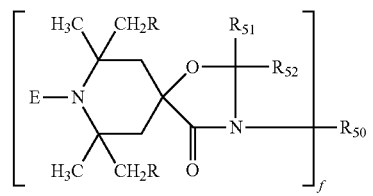
(T)
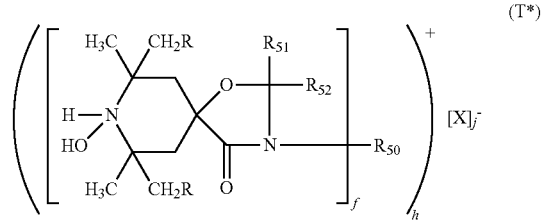
(T*)
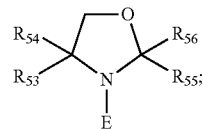
(U)
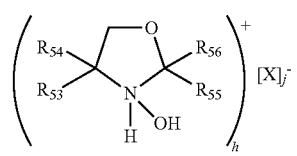
(U*)
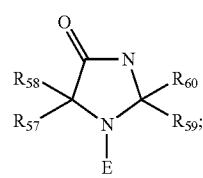
(V)
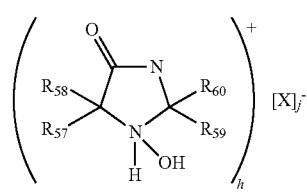
(V*)
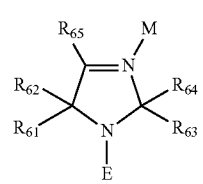
(W)
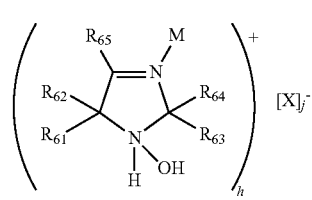
(W*)

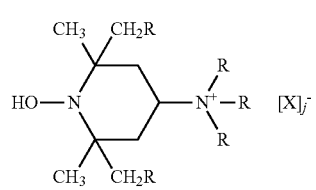 (X)
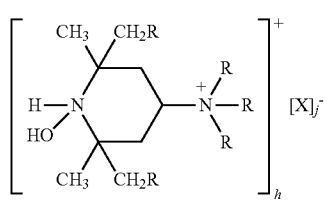 (X*)
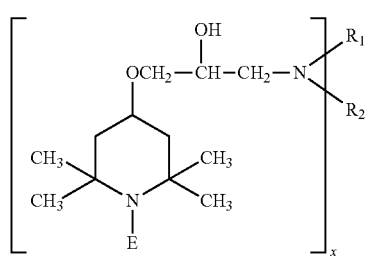 (Y)
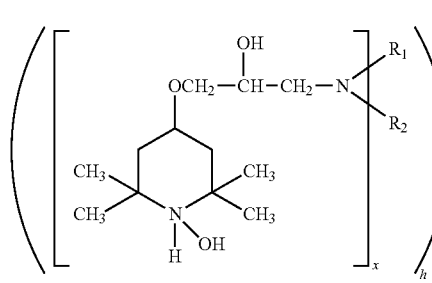 (Y*)
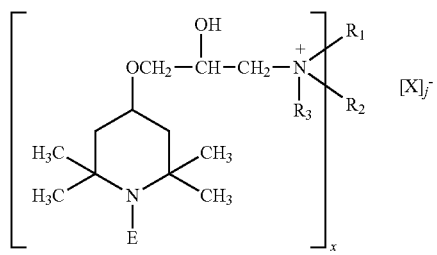 (Z)
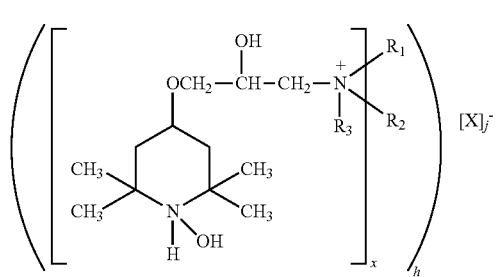 (Z*)
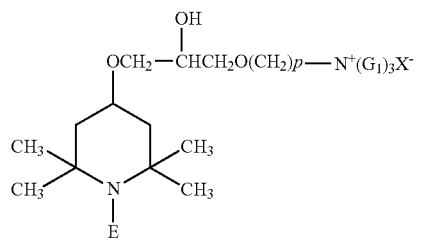 (AA)
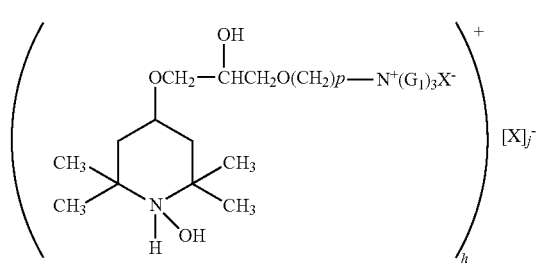 (AA*)
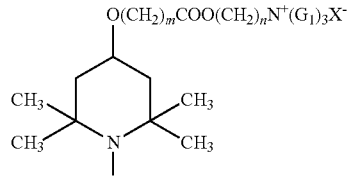 (BB)
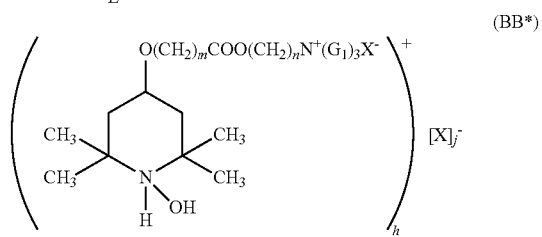 (BB*)
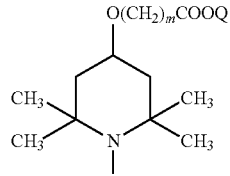 (CC)
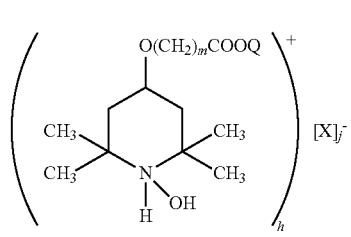 (CC*)
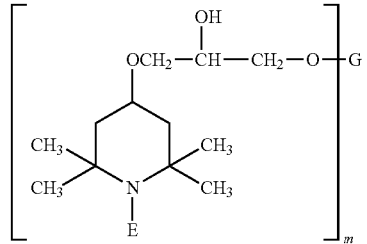 (DD)

-continued (DD*)

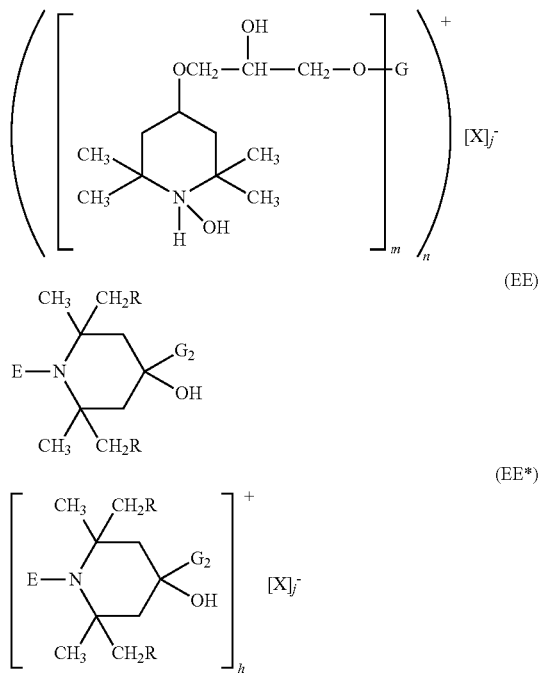

(EE)

(EE*)

wherein
E is oxyl or hydroxyl,
R is hydrogen or methyl,
in formula A and A*,
n is 1 or 2,
when n is 1,
$R_1$ is hydrogen, alkyl of 1 to 18 carbon atoms, alkenyl of 2-18 carbon atoms, propargyl, glycidyl, alkyl of 2 to 50 carbon atoms interrupted by one to twenty oxygen atoms, said alkyl substituted by one to ten hydroxyl groups or both interrupted by said oxygen atoms and substituted by said hydroxyl groups, or
$R_1$ is alkyl of 1 to 4 carbon atoms substituted by a carboxy group or by —COOZ where Z is hydrogen, alkyl of 1 to 4 carbon atoms or phenyl, or where Z is said alkyl substituted by —(COO$^-$)$_n$M$^{n+}$ where n is 1-3 and M is a metal ion from the 1st, 2nd or 3rd group of the periodic table or is Zn, Cu, Ni or Co, or M is a group N'(R$_2$)$_4$ where $R_2$ is alkyl of 1 to 8 carbon atoms or benzyl,
when n is 2,
$R_1$ is alkylene of 1 to 12 carbon atoms, alkenylene of 4 to 12 carbon atoms, xylylene or alkylene of 1 to 50 carbon atoms interrupted by one to twenty oxygen atoms, substituted by one to ten hydroxyl groups or both interrupted by said oxygen atoms and substituted by said hydroxyl groups,
in formula B and B*,
m is 1 to 4,
when m is 1,
$R_2$ is alkyl of 1 to 18 carbon atoms, alkyl of 3 to 18 carbon atoms interrupted by —COO—, or
$R_2$ is —CH$_2$(OCH$_2$CH$_2$)$_n$OCH$_3$ where n is 1 to 12, or
$R_2$ is cycloalkyl of 5 to 12 carbon atoms, aryl of 6 to 12 carbon atoms, or said aryl substituted by one to four alkyl groups of 1 to 4 carbon atoms, or
$R_2$ is —NHR$_3$ where $R_3$ is alkyl of 1 to 18 carbon atoms, cycloalkyl of 5 to 12 carbon atoms, aryl of 6 to 12 carbon atoms, or said aryl substituted by one to four alkyl of 1 to 4 carbon atoms, or $R_2$ is —N(R$_3$)$_2$ where $R_3$ is as defined above,
when m is 2,
$R_2$ is alkylene of 1 to 12 carbon atoms, alkenylene of 4 to 12 carbon atoms, xylylene, alkylene of 2 to 12 carbon atoms interrupted by —COO—, or $R_2$ is —CH$_2$(OCH$_2$CH$_2$)$_n$OCH$_2$— where n is 1 to 12, or
$R_2$ is cycloalkylene of 5 to 12 carbon atoms, aralkylene of 7 to 15 carbon atoms or arylene of 6 to 12 carbon atoms, or
$R_2$ is —NHR$_4$NH— where $R_4$ is alkylene of 2 to 18 carbon atoms, cycloalkylene of 5 to 12 carbon atoms, aralkylene of 8 to 15 carbon atoms or arylene of 6 to 12 carbon atoms, or
$R_2$ is —N(R$_3$)R$_4$N(R$_3$)— where $R_3$ and $R_4$ are as defined above, or
$R_2$ is —CO— or —NH—CO—NH—,
when m is 3,
$R_2$ is alkanetriyl of 3 to 8 carbon atoms or benzenetriyl, or
when m is 4,
$R_2$ is alkanetetrayl of 5 to 8 carbon atoms or benzenetetrayl,
in formula C and C*,
$R_{10}$ is hydrogen, alkyl of 1 to 18 carbon atoms, cycloalkyl of 5 to 12 carbon atoms, aralkyl of 7 to 15 carbon atoms, alkanoyl of 2 to 18 carbon atoms, alkenoyl of 3 to 5 carbon atoms or benzoyl,
x is 1 or 2,
when x is 1,
$R_{11}$ is hydrogen, alkyl of 1 to 18 carbon atoms, alkenyl of 2 to 18 carbon atoms, propargyl, glycidyl, alkyl of 2 to 50 carbon atoms interrupted by one to twenty oxygen atoms, said alkyl substituted by one to ten hydroxyl groups or both interrupted by said oxygen atoms and substituted by said hydroxyl groups, or
$R_{11}$ is alkyl of 1 to 4 carbon atoms substituted by a carboxy group or by —COOZ where Z is hydrogen, alkyl of 1 to 4 carbon atoms or phenyl, or where Z is said alkyl substituted by —(COO$^-$)$_n$M$^{n+}$ where n is 1-3 and M is a metal ion from the 1st, 2nd or 3rd group of the periodic table or is Zn, Cu, Ni or Co, or M is a group N$''^+$(R$_2$)$_4$ where $R_2$ is hydrogen, alkyl of 1 to 8 carbon atoms or benzyl, or
when x is 2,
$R_{11}$ is alkylene of 1 to 12 carbon atoms, alkenylene of 4 to 12 carbon atoms, xylylene or alkylene of 1 to 50 carbon atoms interrupted by one to twenty oxygen atoms, substituted by one to ten hydroxyl groups or both interrupted by said oxygen atoms and substituted by said hydroxyl groups,
in formula D and D*,
$R_{10}$ is as defined above,
y is 1 to 4, and
$R_{12}$ is defined as $R_2$ above
in formula E and E*,
k is 1 or 2,
when k is 1,
$R_{20}$ and $R_{21}$ are independently alkyl of 1 to 12 carbon atoms, alkenyl of 2 to 12 carbon atoms or aralkyl of 7 to 15 carbon atoms, or $R_{20}$ is also hydrogen, or
$R_{20}$ and $R_{21}$ together are alkylene of 2 to 8 carbon atoms or said alkylene substituted by hydroxyl, or are acyloxyalkylene of 4 to 22 carbon atoms, or
when k is 2,
$R_{20}$ and $R_{21}$ are together (—CH$_2$)$_2$C(CH$_2$—)$_2$,
in formula F and F*,
$R_{30}$ is hydrogen, alkyl of 1 to 18 carbon atoms, benzyl, glycidyl, or alkoxyalkyl of 2 to 6 carbon atoms,
g is 1 or 2,
when g is 1, $R_{31}$ is defined as $R_1$ above when n is 1, when g is 2, $R_{31}$ is defined as $R_1$ above when n is 2,
in formula G and G*,
$Q_1$ is —$NR_{41}$— or —O—,
$E_1$ is alkylene of 1 to 3 carbon atoms, or $E_1$ is —$CH_2$—CH($R_{42}$)—O— where $R_{42}$ is hydrogen, methyl or phenyl, or $E_1$ is —$(CH_2)_3$—NH— or $E_1$ is a direct bond,
$R_{40}$ is hydrogen or alkyl of 1 to 18 carbon atoms,
$R_{41}$ is hydrogen, alkyl of 1 to 18 carbon atoms, cycloalkyl of 5 to 12 carbon atoms, aralkyl of 7 to 15 carbon atoms, aryl of 6 to 10 carbon atoms, or $R_{41}$ is —$CH_2$—CH($R_{42}$)—OH where $R_{42}$ is as defined above,
in formula H and H*,
p is 1 or 2,
$T_4$ is as defined for $R_{11}$ when x is 1 or 2,
M and Y are independently methylene or carbonyl, for instance M is methylene and Y is carbonyl,
in formula I and I*,
this formula denotes a recurring structural unit of a polymer where $T_1$ is ethylene or 1,2-propylene or is the repeating structural unit derived from an alpha-olefin copolymer with an alkyl acrylate or methacrylate, and where
q is 2 to 100,
$Q_1$ is —$N(R_{41})$— or —O— where $R_{41}$ is as defined above,
in formula J and J*,
r is 1 or 2,
$T_7$ is as defined for $R_1$ when n is 1 or 2 in formula A,
for example $T_7$ is octamethylene when r is 2,
in formula L and L*,
u is 1 or 2,
$T_{13}$ is as defined for $R_1$ when n is 1 or 2 in formula A, with the proviso that $T_{13}$ is not hydrogen when u is 1,
in formula M and M*,
$E_1$ and $E_2$, being different, each are —CO— or —$N(E_5)$- where $E_5$ is hydrogen, alkyl of 1 to 12 carbon atoms or alkoxycarbonylalkyl of 4 to 22 carbon atoms, for instance $E_1$ is —CO— and $E_2$ is —$N(E_5)$-,
$E_3$ is hydrogen, alkyl of 1 to 30 carbon atoms, phenyl, naphthyl, said phenyl or said naphthyl substituted by chlorine or by alkyl of 1 to 4 carbon atoms, or phenylalkyl of 7 to 12 carbon atoms, or said phenylalkyl substituted by alkyl of 1 to 4 carbon atoms,
$E_4$ is hydrogen, alkyl of 1 to 30 carbon atoms, phenyl, naphthyl or phenylalkyl of 7 to 12 carbon atoms, or
$E_3$ and $E_4$ together are polymethylene of 4 to 17 carbon atoms, or said polymethylene substituted by one to four alkyl of 1 to 4 carbon atoms, for example methyl,
in formula N,
$R_1$ is as defined for $R_1$ in formula A when n is 1,
$G_3$ is a direct bond, alkylene of 1 to 12 carbon atoms, phenylene or —NH-$G_1$-NH— where $G_1$ is alkylene of 1 to 12 carbon atoms,
in formula O and O*,
$R_{10}$ is as defined for $R_{10}$ in formula C,
in formula P and P*,
$E_6$ is an aliphtic or aromatic tetravalent radical, for example neopentanetetrayl or benzenetetrayl,
in formula T and T*,
$R_{51}$ is hydrogen, alkyl of 1 to 18 carbon atoms, cycloalkyl of 5 to 12 carbon atoms, or aryl of 6 to 10 carbon atoms,
$R_{52}$ is hydrogen or alkyl of 1 to 18 carbon atoms, or
$R_{51}$ and $R_{52}$ together of alkylene of 4 to 8 carbon atoms,
f is 1 or 2,
when f is 1,
$R_{50}$ is as defined for $R_{11}$ in formula C when x is 1, or $R_{50}$ is —$(CH_2)_z COOR_{54}$ where z is 1 to 4 and $R_{54}$ is hydrogen or alkyl of 1 to 18 carbon atoms, or $R_{54}$ is a metal ion from the 1st, 2nd or 3rd group of the periodic table or a group —$N(R_{55})_4$ where $R_{55}$ is hydrogen, alkyl of 1 to 12 carbon atoms or benzyl,
when f is 2, $R_{50}$ is as defined for $R_{11}$ in formula C when x is 2,
in formula U and U*,
$R_{53}$, $R_{54}$, $R_{55}$ and $R_{56}$ are independently alkyl of 1 to 4 carbon atoms or are together pentamethylene.
in formula V and V*,
$R_{57}$, $R_{58}$, $R_{59}$ and $R_{60}$ are independently alkyl of 1 to 4 carbon atoms or are together pentamethylene.
in formula W and W*,
$R_{61}$, $R_{62}$, $R_{63}$ and $R_{64}$ are independently alkyl of 1 to 4 carbon atoms or are together pentamethylene,
$R_{65}$ is alkyl of 1 to 5 carbon atoms,
M is hydrogen or oxygen,
wherein in formulas X to CC and X* to CC*
n is 2 to 3,
$G_1$ is hydrogen, methyl, ethyl, butyl or benzyl,
m is 1 to 4,
x is 1 to 4,
when x is 1,
$R_1$ and $R_2$ are independently alkyl of 1 to 18 carbon atoms, said alkyl interrupted by one to five oxygen atoms, said alkyl substituted by 1 to 5 hydroxyl groups or said alkyl both interrupted by said oxygen atoms and substituted by said hydroxyl groups; cycloalkyl of 5 to 12 carbon atoms, aralkyl of 7 to 15 carbon atoms, aryl of 6 to 10 carbon atoms or said aryl substituted by one to three alkyl of 1 to 8 carbon atoms, or $R_1$ is also hydrogen,
or $R_1$ and $R_2$ are together tetramethylene, pentamethylene, hexamethylene or 3-oxapentamethylene,
when x is 2,
$R_1$ is hydrogen, alkyl of 1 to 8 carbon atoms, said alkyl interrupted by one or two oxygen atoms, said alkyl substituted by a hydroxyl group, or said alkyl both interrupted by one or two oxygen atoms and substituted by a hydroxyl group,
$R_2$ is alkylene of 2 to 18 carbon atoms, said alkylene interrupted by one to five oxygen atoms, said alkylene substituted by 1 to 5 hydroxyl groups or said alkylene both interrupted by said oxygen atoms and substituted by said hydroxyl groups; o-, m- or p-phenylene or said phenylene substituted by one or two alkyl of 1 to 4 carbon atoms, or
$R_2$ is —$(CH_2)_k O[(CH_2)_k O]_h (CH_2)_k$— where k is 2 to 4 and h is 1 to 40, or
$R_1$ and $R_2$ together with the two N atoms to which they are attached are piperazin-1,4-diyl,
when x is 3,
$R_1$ is hydrogen
$R_2$ is alkylene of 4 to 8 carbon atoms interrupted by one nitrogen atom,
when x is 4,
$R_1$ is hydrogen,
$R_2$ is alkylene of 6 to 12 carbon atoms interrupted by two nitrogen atoms,
$R_3$ is hydrogen, alkyl of 1 to 8 carbon atoms, said alkyl interrupted by one or two oxygen atoms, said alkyl substituted by a hydroxyl group, or both interrupted by one or two oxygen atoms and substituted by a hydroxyl group,
P is 2 or 3, and
Q is an alkali metal salt, ammonium or $N^+(G_1)_4$,
in formula DD and DD*
m is 2 or 3,
when m is 2, G is —(CH$_2$CHR—O)$_r$CH$_2$CHR—, where r is 0 to 3, and R is hydrogen or methyl, and
when m is 3,
G is glyceryl,
in formula EE and EE*
G$_2$ is —CN, —CONH$_2$ or —COOG$_3$ where G$_3$ is hydrogen, alkyl of 1 to 18 carbon atoms or phenyl,
X is an inorganic or organic anion, such as phosphate, phosphonate, carbonate, bicarbonate, nitrate, chloride, bromide, bisulfite, sulfite, bisulfate, sulfate, borate, formate, acetate, benzoate, citrate, oxalate, tartrate, acrylate, polyacrylate, fumarate, maleate, itaconate, glycolate, gluconate, malate, mandelate, tiglate, ascorbate, polymethacrylate, a carboxylate of nitrilotriacetic acid, hydroxyethylethylenediaminetriacetic acid, ethylenediaminetetraacetic acid or of diethylenetriaminepentaacetic acid, a diethylenetriaminepentamethylenephosphonate, an alkylsulfonate or an arylsulfonate, and
where the total charge of cations h is equal to the total charge of anions j.

For example, the compounds (3) are those of formulas A, A*, B, B*, C, C*, D, D*, Q, Q*, R, R*, S, S*, X, X*, Y, Y*, Z and Z*,
R is hydrogen,
in formula A and A*
n is 1 or 2,
when n is 1,
R$_1$ is hydrogen, alkyl of 1 to 6 carbon atoms, alkenyl of 2-6 carbon atoms, propargyl, glycidyl, alkyl of 2 to 20 carbon atoms interrupted by one to ten oxygen atoms, said alkyl substituted by one to five hydroxyl groups or both interrupted by said oxygen atoms and substituted by said hydroxyl groups, or
R$_1$ is alkyl of 1 to 4 carbon atoms substituted by a carboxy group or by —COOZ where Z is hydrogen or alkyl of 1 to 4 carbon atoms,
when n is 2,
R$_1$ is alkylene of 1 to 8 carbon atoms, alkenylene of 4 to 8 carbon atoms, alkylene of 1 to 20 carbon atoms interrupted by one to ten oxygen atoms, substituted by one to five hydroxyl groups or both interrupted by said oxygen atoms and substituted by said hydroxyl groups,
in formula B and B*
m is 1 or 2
when m is 1,
R$_2$ is alkyl of 1 to 4 carbon atoms or R$_2$ is CH$_2$(OCH$_2$CH$_2$)$_n$OCH$_3$ where n is 1 to 12, or
R$_2$ is phenyl, or said phenyl substituted by one to three methyl groups,
R$_2$ is —NHR$_3$ where R$_3$ is alkyl of 1 to 4 carbon atoms or phenyl, or said phenyl substituted by one or two methyl groups,
when m is 2,
R$_2$ is alkylene of 1 to 8 carbon atoms, alkenylene of 4 to 8 carbon atoms, or R$_2$ is —CH$_2$(OCH$_2$CH$_2$)$_n$OCH$_2$— where n is 1 to 12,
R$_2$ is NHR$_4$NH where R$_4$ is of 2 to 6 carbon atoms, aralkylene of 8 to 15 carbon atoms or arylene of 6 to 12 carbon atoms,
R$_2$ is —CO— or —NHCONH,
in formula C and C*,
R$_{10}$ is hydrogen or, alkanoyl of 1 to 3 carbon atoms,
x is 1 or 2,
when x is 1,
R$_{11}$ is hydrogen, alkyl of 1 to 6 carbon atoms or glycidyl,
R$_{11}$ is alkyl of 1 to 4 carbon atoms substituted by a carboxy group or by COOZ where Z is hydrogen or alkyl of 1 to 4 carbon atoms,
when x is 2,
R$_{11}$ is alkylene of 1 to 6 carbon atoms,
in formula D and D*,
R$_{10}$ is hydrogen,
y is 1 or 2,
R$_{12}$ is defined as R$_2$ above,
in formula Y, Y*, Z and Z*,
x is 1 or 2,
when x is 1,
R$_1$ and R$_2$ are independently alkyl of 1 to 4 carbon atoms, or R$_1$ and R$_2$ are together tetramethylene, or pentamethylene,
R$_2$ is hydrogen or alkyl of 1 to 4 carbon atoms, said alkyl group substituted by a hydroxyl group,
when x is 2,
R$_1$ is hydrogen, alkyl of 1 to 4 carbon atoms, said alkyl substituted by a hydroxyl group,
R$_2$ is alkylene of 2 to 6 carbon atoms,
R$_3$ is as defined above.

For instance, the compounds (3) are those of formulas A, A*, B, B*, C, C*, D, D*, Q, Q*, R and R*,
R is hydrogen,
in formula A and A*,
h is 1,
R$_1$ is hydrogen, alkyl of 1 to 4 carbon atoms, glycidyl, alkyl of 2 to 4 carbon atoms interrupted by one or two oxygen atoms, said alkyl substituted by one or two hydroxyl groups or both interrupted by said oxygen atoms and substituted by said hydroxyl groups, or
R$_1$ is alkyl of 1 to 4 carbon atoms substituted by —COOZ where Z is hydrogen or alkyl of 1 to 4 carbon atoms,
in formula B and B*,
m is 1 or 2,
R$_2$ is alkyl of 1 to 4 carbon atoms or R$_2$ is CH$_2$(OCH$_2$CH$_2$)$_n$OCH$_3$ where n is 1 to 4,
when m is 2,
R$_2$ is alkylene of 1 to 8 carbon atoms,
in formula C and C*,
R$_{10}$ is hydrogen or alkanoyl of 1 or 2 carbon atoms,
x is 1 or 2,
when x is 1,
R$_{11}$ is hydrogen, alkyl of 1 to 4 carbon atoms or glycidyl,
R$_{11}$ is alkyl of 1 to 4 carbon atoms substituted by COOZ where Z is hydrogen or alkyl of 1 to 4 carbon atoms,
when x is 2,
R$_{11}$ is alkylene of 1 to 6 carbon atoms,
in formula D and D*,
R$_{10}$ is hydrogen,
y is 1 or 2,
R$_{12}$ is defined as R$_2$ above.

The selected hindered nitroxyl, hydroxylamine and hydroxylamine salt compound (3) preferably conforms to the formula

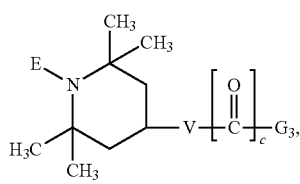

where E is oxyl or hydroxyl and $G_3$, V, c are as defined for formula (1), or a salt thereof.

Compounds (3), such as those of formulae A to EE, especially those of the above formula (3), may be used as such or in form of suitable acid addition salts, as indicated, for example, in the above formulae A* to EE*. These are, for example, salts of pharmaceutically acceptable inorganic or organic acids. Useful acid addition salts include those with inorganic acids, such as chlorides or sulfates, or with organic acids, e.g. sulfonic or carbonic acids, e.g. as hydrogen (or, where appropriate, dihydrogen) phosphate, phosphonate, carbonate, bicarbonate, nitrate, chloride, bromide, bisulfite, sulfite, bisulfate, sulfate, borate, formate, acetate, benzoate, citrate, oxalate, tartrate, acrylate, polyacrylate, fumarate, maleate, itaconate, glycolate, gluconate, pyruvate, malate, mandelate, tiglate, ascorbate, polymethacrylate, a carboxylate of nitrilotriacetic acid, hydroxyethylethylenediaminetriacetic acid, ethylenediaminetetraacetic acid or of diethylenetriaminepentaacetic acid, a diethylenetriaminepentamethylenephosphonate, an alkylsulfonate or an arylsulfonate, such as methane sulfonates, benzoates, oxalates or acetates, where appropriate and expedient; these ions also correspond to preferred meanings of X. The salts are preferably pharmaceutically acceptable salts. Pharmaceutically acceptable salts are salts of acids mostly known in the art, e.g. of acids like alkanecarboxylic acids (especially of $C_1$-$C_4$acids); di- or polycarboxylic and/or hydroxycarboxylic acids such as oxalic, malonic, succinic, fumaric, citric, maleic, tartaric, lactic acid, glucuronic acid and other acids derived from sugars, each of these acids in both enantiomeric forms where optically active; phosphoric, sulfuric, methylsulfonic, toluenesulfonic, benzoic acid; some preferred salts include hydrochlorides, hydrobromides, hydroiodides, benzoates, phosphates, hydrogenphosphates, sulfates, hydrogensulfates and especially citrates. Preferred are, for example, citrates, hydrochlorides, oxalates.

$C_1$-$C_{22}$Alkyl is straight-chain or branched alkyl radicals, such as methyl, ethyl, n-propyl, isopropyl, n-butyl, sec-butyl, tert-butyl, amyl, isoamyl or tert-amyl, heptyl, octyl, isooctyl, nonyl, decyl, undecyl, dodecyl, tetradecyl, pentadecyl, hexadecyl, heptadecyl, octadecyl or eicosyl.

$C_1$-$C_{22}$Alkylthio is straight-chain or branched alkylthio radicals, such as methylthio, ethylthio, n-propylthio, isopropylthio, n-butylthio, sec-butylthio, tert-butylthio, amylthio, heptylthio, octylthio, isooctylthio, nonylthio, decylthio, undecylthio, dodecylthio, tetradecylthio, pentadecylthio, hexadecylthio, heptadecylthio, octadecylthio or eicosylthio.

$C_2$-$C_{22}$Alkylthioalkyl is alkylthio as described above attached by its sulfur atom to alkyl, where the total residue contains 2-22 carbon atoms.

$C_2$-$C_{18}$Alkenyl is, for example, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_5$-$C_7$Cycloalkyl is cyclopentyl, cycloheptyl or, preferably, cyclohexyl.

$C_7$-$C_9$-Phenylalkyl includes phenylpropyl (such as cumyl), phenylethyl and, preferably, benzyl.

M as alkali often is Li, Na, K, Cs.

Useful compounds of present formulae (1) and (2) include those listed in Table 1:

TABLE 1

| compound of formula | |
|---|---|
| (7) |  |
| (8) |  |
| (9) |  |

TABLE 1-continued
| compound of formula | |
|---|---|
| (10) | 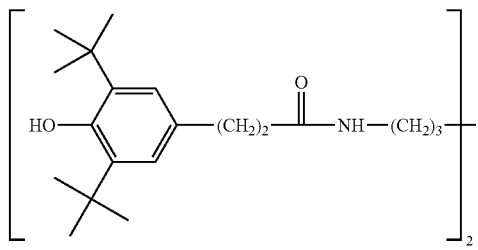 |
| (11) | 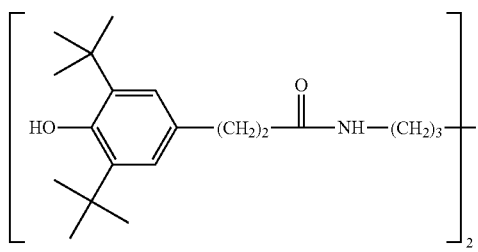 |
| (12) | 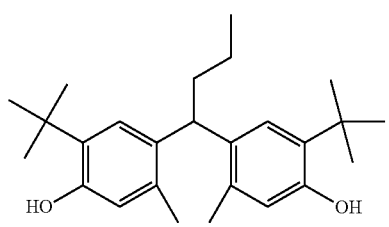 [SMILES: CCCC(c1cc(C(C)(C)C)c(O)cc1C)c1cc(C(C)(C)C)c(O)cc1C] |
| (13) | 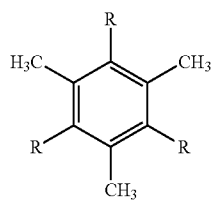<br>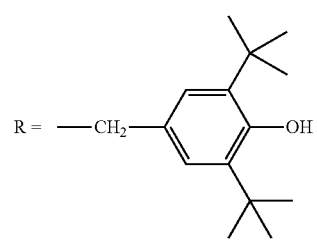 |
| (14) | 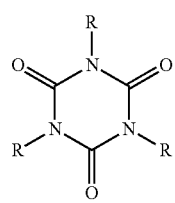 |

TABLE 1-continued
compound of formula
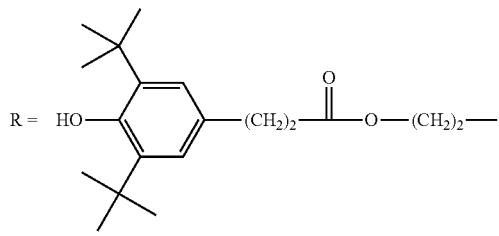
(15) 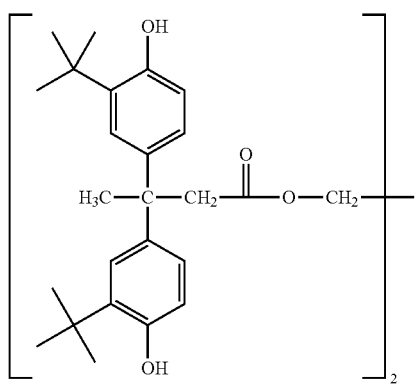
(16) 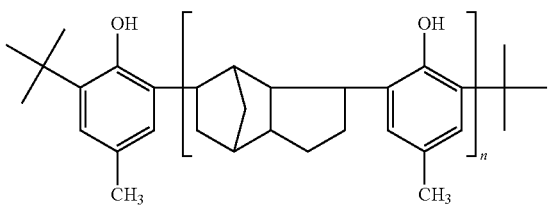
n = 1-3
(17) 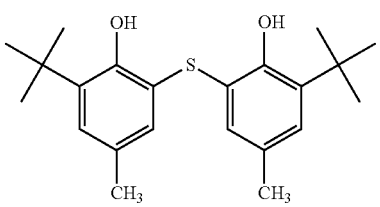 [SMILES: Cc1cc(Sc2cc(C)cc(C(C)(C)C)c2O)c(O)c(C(C)(C)C)c1]
(18) 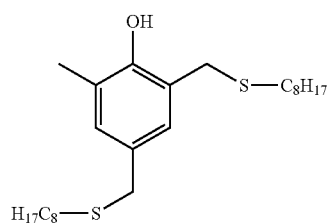
(19) 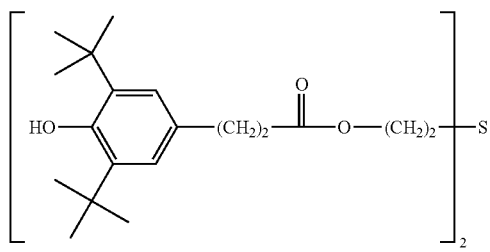

TABLE 1-continued
| compound of formula | |
|---|---|
| (20) | 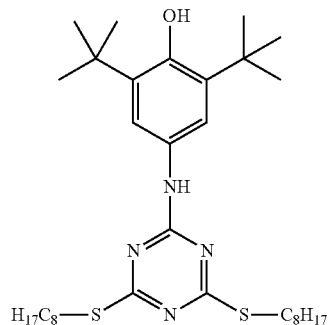 |
| (21) | 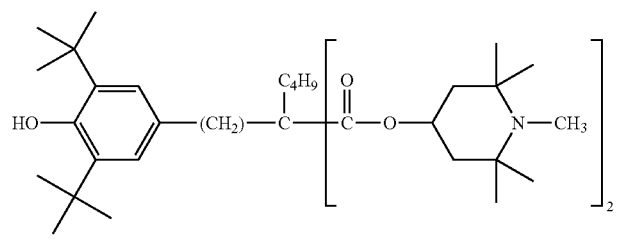 |
| (22) | 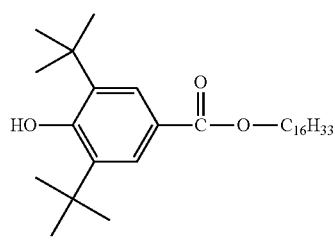 |
| (23) | 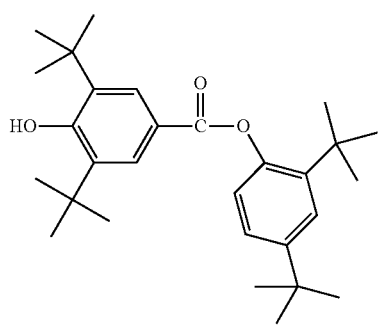 [SMILES: CC(C)(C)c1ccc(OC(=O)c2cc(C(C)(C)C)c(O)c(C(C)(C)C)c2)c(C(C)(C)C)c1] |
| (24) | 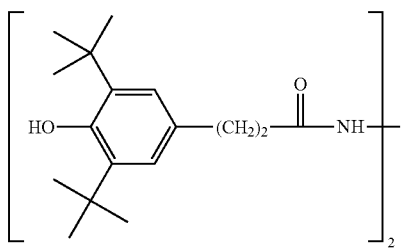 |

TABLE 1-continued
| compound of formula | |
|---|---|
| (25) | 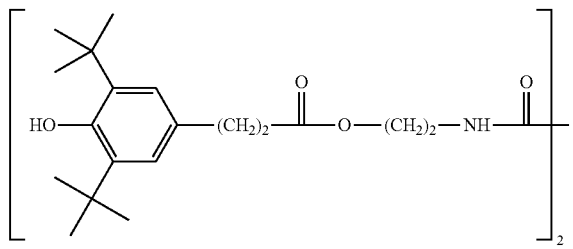 |
| (26) | 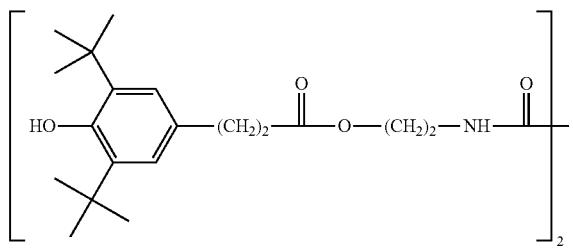 |
| (27) | 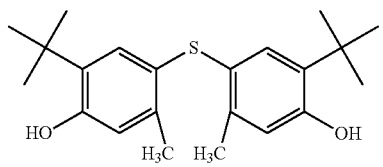 [SMILES: Cc1cc(O)c(C(C)(C)C)cc1Sc1cc(C(C)(C)C)c(O)cc1C] |
| (28) | 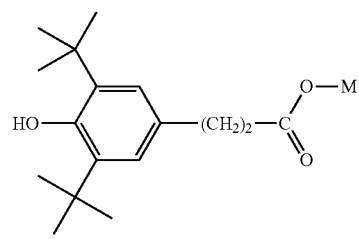
M = H, ammonium, alkali |
| (29) | 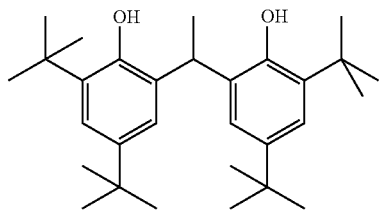 [SMILES: CC(c1cc(C(C)(C)C)cc(C(C)(C)C)c1O)c1cc(C(C)(C)C)cc(C(C)(C)C)c1O] |
| (30) | 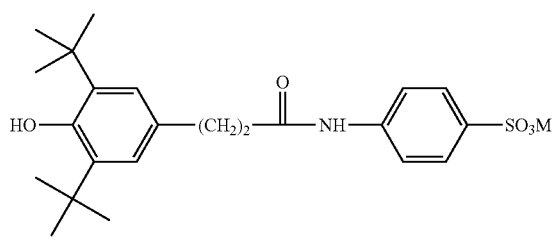
M = H, Na |

TABLE 1-continued

| compound of formula | |
|---|---|
| (31) | [structure: 3,5-di-tert-butyl-4-hydroxyphenyl—(CH₂)₂—C(=O)—O—(CH₂)₂—]₄C |
| (32) | [structure: 3,5-di-tert-butyl-4-hydroxyphenyl—(CH₂)₂—C(=O)—O—C₁₈H₃₇] |
| (33) | [structure: tetrakis(3,5-di-tert-butyl-4-hydroxybenzyl) substituted compound with central methylated benzene and CH₂-linked phenol] |

Useful hindered amine compounds (3) include the following ones: hindered nitroxyl, hydroxylamine and hydroxylamine salt compounds selected from bis(1-oxyl-2,2-6-6-tetramethylpiperidin-4-yl)sebacate; bis(1-hydroxy-2,2-6-6-tetramethylpiperidin-4-yl)sebacate; 1-hydroxy-2,2-6-6-tetramethyl-4-acetoxypiperidinium citrate; 1-oxyl-2,2,6,6-tetramethyl-4-acetamidopiperidine; 1-hydroxy-2,2,6,6-tetramethyl-4-acetamidopiperidine; 1-hydroxy-2,2,6,6-tetramethyl-4-acetamidopiperidinium bisulfate; 1-oxyl-2,2,6,6-tetramethyl-4-oxo-piperidine; 1-hydroxy-2,2,6,6-tetramethyl-4-oxo-piperidine; 1-hydroxy-2,2,6,6-tetramethyl-4-oxo-piperidinium acetate; 1-oxyl-2,2,6,6-tetramethyl-4-methoxy-piperidine; 1-hydroxy-2,2,6,6-tetramethyl-4-methoxy-piperidine; 1-hydroxyl-2,2,6,6-tetramethyl-4-methoxy-piperidinium acetate; 1-oxyl-2,2,6,6-tetramethyl-4-acetoxypiperidine; 1-hydroxy-2,2,6,6-tetramethyl-4-acetoxypiperidine; 1-oxyl-2,2,6,6-tetramethyl-4-propoxy-piperidine; 1-hydroxy-2,2,6,6-tetramethyl-4-propoxy-piperidinium acetate; 1-hydroxy-2,2,6,6-tetramethyl-4-propoxy-piperidine; 1-oxyl-2,2,6,6-tetramethyl-4-(2-hydroxy-4-oxapentoxy)piperidine; 1-hydroxy-2,2,6,6-tetramethyl-4-(2-hydroxy-4-oxapentoxy)piperidinium acetate; 1-oxyl-2,2,6,6-tetramethyl-4-hydroxypiperidine; 1-hydroxy-2,2,6,6-tetramethyl-4-hydroxypiperidine; 1-hydroxy-2,2,6,6-tetramethyl-4-hydroxypiperidinium chloride; 1-hydroxy-2,2,6,6-tetramethyl-4-hydroxypiperidinium acetate; 1-hydroxy-2,2,6,6-tetramethyl-4-hydroxypiperidinium bisulfate; 1-hydroxy-2,2,6,6-tetramethyl-4-hydroxypiperidinium citrate; bis(1-hydroxy-2,2,6,6-tetramethyl-4-hydroxypiperidinium)citrate; tris(1-hydroxy-2,2,6,6-tetramethyl-4-hydroxypiperidinium)citrate; tetra(1-hydroxy-2,2,6,6-tetramethyl-4-hydroxypiperidinium) ethylenediaminetetraacetate; tetra(1-hydroxy-2,2,6,6-tetramethyl-4-acetamidopiperidinium) ethylenediaminetetraacetate; tetra(1-hydroxy-2,2,6,6-tetramethyl-4-oxopiperidinium) ethylenediaminetetraacetate; penta(1-hydroxy-2,2,6,6-tetramethyl-4-hydroxypiperidinium) diethylenetriaminepentaacetate; penta(1-hydroxy-2,2,6,6-tetramethyl-4-acetamidopiperidinium) diethylenetriaminepentaacetate; penta(1-hydroxy-2,2,6,6-tetramethyl-4-oxopiperidinium) diethylenetriaminepentaacetate; tri(1-hydroxy-2,2,6,6-tetramethyl-4-hydroxypiperidinium)nitrilotriacetate; tri(1-hydroxy-2,2,6,6-tetramethyl-4-acetamidopiperidinium) nitrilotriacetate; tri(1-hydroxy-2,2,6,6-tetramethyl-4-oxopiperidinium)nitrilotriacetate; penta(1-hydroxy-2,2,6,6-tetramethyl-4-hydroxypiperidinium) diethylenetriaminepentamethylenephosphonate; penta(1-hydroxy-2,2,6,6-tetramethyl-4-acetamidopiperidinium) diethylenetriaminepentamethylenephosphonate; and penta (1-hydroxy-2,2,6,6-tetramethyl-4-oxopiperidinium) diethylenetriaminepentamethylenephosphonate.

Preferred hindered nitroxyl, hydroxylamine and hydroxylamine salt compounds of formula (3) are selected from 1-oxyl-2,2,6,6-tetramethyl-4-hydroxypiperidine; 1-hydroxy-2,2,6,6-tetramethyl-4-hydroxypiperidine; 1-hydroxy-2,2,6,6-tetramethyl-4-hydroxypiperidinium chloride; 1-hydroxy-2,2,6,6-tetramethyl-4-hydroxypiperidinium acetate; 1-hydroxy-2,2,6,6-tetramethyl-4-hydroxypiperidinium bisulfate; 1-hydroxy-2,2,6,6-tetramethyl-4-hydroxypiperidinium citrate; bis(1-hydroxy-2,2,6,6-tetramethyl-4-hydroxypiperidinium)citrate; tris(1-hydroxy-2,2,6,6-tetramethyl-4-hydroxypiperidinium)citrate; tetra(1-hydroxy-2,2,6,6-tetramethyl-4-hydroxypiperidinium) ethylenediaminetetraacetate; tetra(1-hydroxy-2,2,6,6-tetramethyl-4-acetamidopiperidinium) ethylenediaminetetraacetate; tetra(1-hydroxy-2,2,6,6-tetramethyl-4-oxopiperidinium) ethylenediaminetetraacetate; penta(1-hydroxy-2,2,6,6-tetramethyl-4-hydroxypiperidinium) diethylenetriaminepentaacetate; penta(1-hydroxy-2,2,6,6-tetramethyl-4-acetamidopiperidinium) diethylenetriaminepentaacetate; and penta(1-hydroxy-2,2,6,6-tetramethyl-4-oxopiperidinium) diethylenetriaminepentaacetate.

For example, the compounds of formula (3) are hydroxylamine salts selected from 1-hydroxy-2,2,6,6-tetramethyl-4-hydroxypiperidinium citrate; bis(1-hydroxy-2,2,6,6-tetramethyl-4-hydroxypiperidinium)citrate; tris(1-hydroxy-2,2,6,6-tetramethyl-4-hydroxypiperidinium)citrate; 1-hydroxy-2,2,6,6-tetramethyl-4-hydroxypiperidinium DTPA; bis(1-hydroxy-2,2,6,6-tetramethyl-4-hydroxypiperidinium) DTPA; tris(1-hydroxy-2,2,6,6-tetramethyl-4-hydroxypiperidinium) DTPA; tetrakis(1-hydroxy-2,2,6,6-tetramethyl-4-hydroxypiperidinium) DTPA; pentakis(1-hydroxy-2,2,6,6-tetramethyl-4-hydroxypiperidinium) DTPA; 1-hydroxy-2,2,6,6-tetramethyl-4-hydroxypiperidinium EDTA; bis(1-hydroxy-2,2,6,6-tetramethyl-4-hydroxypiperidinium) EDTA; tris(1-hydroxy-2,2,6,6-tetramethyl-4-hydroxypiperidinium) EDTA; tetrakis(1-hydroxy-2,2,6,6-tetramethyl-4-hydroxypiperidinium) EDTA; 1-hydroxy-2,2,6,6-tetramethyl-4-oxo-piperidinium citrate; bis(1-hydroxy-2,2,6,6-tetramethyl-4-oxo-piperidinium)citrate; tris(1-hydroxy-2,2,6,6-tetramethyl-4-oxo-piperidinium)citrate; 1-hydroxy-2,2,6,6-tetramethyl-4-oxo-piperidinium DTPA; bis(1-hydroxy-2,2,6,6-tetramethyl-4-oxo-piperidinium) DTPA; tris(1-hydroxy-2,2,6,6-tetramethyl-4-oxo-piperidinium) DTPA; tetrakis(1-hydroxy-2,2,6,6-tetramethyl-4-oxo-piperidinium) DTPA; pentakis(1-hydroxy-2,2,6,6-tetramethyl-4-oxo-piperidinium) DTPA; 1-hydroxy-2,2,6,6-tetramethyl-4-oxo-piperidinium EDTA; bis(1-hydroxy-2,2,6,6-tetramethyl-4-oxo-piperidinium) EDTA; tris(1-hydroxy-2,2,6,6-tetramethyl-4-oxo-piperidinium) EDTA; tetrakis(1-hydroxy-2,2,6,6-tetramethyl-4-oxo-piperidinium) EDTA; 1-hydroxy-2,2,6,6-tetramethyl-4-acetamidopiperidinium citrate; bis(1-hydroxy-2,2,6,6-tetramethyl-4-acetamidopiperidinium)citrate; tris(1-hydroxy-2,2,6,6-tetramethyl-4-acetamidopiperidinium)citrate; 1-hydroxy-2,2,6,6-tetramethyl-4-acetamidopiperidinium DTPA; bis(1-hydroxy-2,2,6,6-tetramethyl-4-acetamidopiperidinium) DTPA; tris(1-hydroxy-2,2,6,6-tetramethyl-4-acetamidopiperidinium) DTPA; tetrakis(1-hydroxy-2,2,6,6-tetramethyl-4-acetamidopiperidinium) DTPA; pentakis(1-hydroxy-2,2,6,6-tetramethyl-4-acetamidopiperidinium) DTPA; 1-hydroxy-2,2,6,6-tetramethyl-4-acetamidopiperidinium EDTA; bis(1-hydroxy-2,2,6,6-tetramethyl-4-acetamidopiperidinium) EDTA; tris(1-hydroxy-2,2,6,6-tetramethyl-4-acetamidopiperidinium) EDTA; tetrakis(1-hydroxy-2,2,6,6-tetramethyl-4-hydroxypiperidinium) EDTA; 1-hydroxy-2,2,6,6-tetramethyl-4-acetoxypiperidinium citrate; bis(1-hydroxy-2,2,6,6-tetramethyl-4-acetoxypiperidinium)citrate; tris(1-hydroxy-2,2,6,6-tetramethyl-4-acetoxypiperidinium)citrate; 1-hydroxy-2,2,6,6-tetramethyl-4-acetoxypiperidinium DTPA; bis(1-hydroxy-2,2,6,6-tetramethyl-4-acetoxypiperidinium) DTPA; tris(1-hydroxy-2,2,6,6-tetramethyl-4-acetoxypiperidinium) DTPA; tetrakis(1-hydroxy-2,2,6,6-tetramethyl-4-acetoxypiperidinium) DTPA; pentakis(1-hydroxy-2,2,6,6-tetramethyl-4-acetoxypiperidinium) DTPA; 1-hydroxy-2,2,6,6-tetramethyl-4-acetoxypiperidinium EDTA; bis(1-hydroxy-2,2,6,6-tetramethyl-4-acetoxypiperidinium) EDTA; tris(1-hydroxy-2,2,6,6-tetramethyl-4-acetoxypiperidinium) EDTA and tetrakis(1-hydroxy-2,2,6,6-tetramethyl-4-acetoxypiperidinium) EDTA.

The above named counter-ions are ethylenediaminetetraacetic acid (EDTA), diethylenetriaminepentaacetic acid (DTPA), hydroxyethylethylenediaminetriacetic acid (HEDTA), nitrilotriacetic acid (NTA) or diethylenetriaminepentamethylenephosphonic acid (DTPMPA).

$G_1$ and $G_2$ preferably are, independently of each other, $C_1$-$C_{18}$alkyl and, in particular, $C_1$-$C_5$alkyl, especially tert.-butyl. In preferred compounds of the formula (1) or (2), $G_1$ is located in meta-position relative to $G_2$.

$G_3$ is most preferred as hydrogen; $C_1$-$C_{22}$alkyl; $SO_3M$; propyl substituted by OH and/or by $C_2$-$C_{22}$alkanoyloxy; a direct bond; —$CH_2$—;

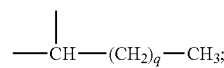

propyl substituted by OH or $C_2$-$C_{22}$alkanoyloxy;

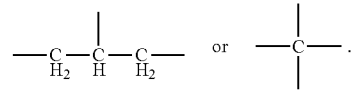

Preferred $G_4$ and $G_5$ independently are H or $C_1$-$C_4$alkyl, especially methyl.

Of specific technical interest are those compounds of the formula (1) containing a thio group, i.e. those wherein $G_1$ and/or $G_3$ are selected from alkylthio, alkylthioalkyl, —S—.

It is preferred to use compounds of formula (1) and/or (2), especially wherein a is 1;

each of b, c, d, e, n, M, q, V is as defined above;

Q, where present, is —$C_mH_{2m}$— and, preferably, a methylene or ethylene radical, T, where present, is —$C_nH_{2n}$— or phenylene;

$G_3$ is hydrogen; $C_1$-$C_{22}$alkyl; $SO_3M$; propyl substituted by OH and/or by $C_2$-$C_{22}$alkanoyloxy;

or $G_3$ is a direct bond; —$CH_2$—;

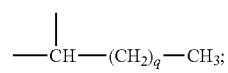

or propyl substituted by OH or $C_2$-$C_{22}$alkanoyloxy;

or $G_3$ is

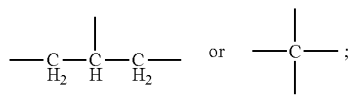

$G_4$ and $G_5$ independently are H or $C_1$-$C_4$alkyl, especially methyl;
most preferred among them are those compounds of the formula (1), wherein
e is 1 or 2 and $G_3$ is $SO_3M$; propyl substituted by OH and/or by $C_2$-$C_{22}$alkanoyloxy;
or $G_3$ is a direct bond; —$CH_2$—;

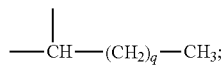

or propyl substituted by OH or $C_2$-$C_{22}$alkanoyloxy; where M is alkali and q is 0 or 1;
or of the formula (2).

Most preferred compound of the formula (3) is of the formula

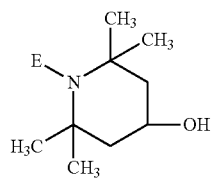

or is an acid addition salt thereof, especially as defined above.

Particularly interesting compounds (I) include those of formula

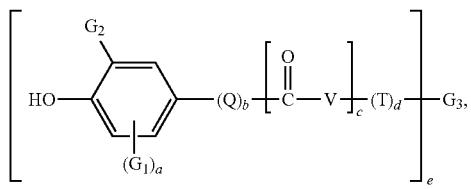

wherein
$G_1$ and $G_2$ are each independently of the other $C_1$-$C_5$alkyl, or $G_1$ and $G_2$ especially are 2,6-di-tert.butyl;
a is 1 or 2, especially 1; and
$G_3$, Q, V, T, b, c, d and e have the meanings cited for formula (1), or especially
b is 1 and Q is ethylene;
c is 1 and V is O or NH;
d is 1 and T is $CH_2$ or phenylene; and
e is 1 and $G_3$ is H, $C_1$-$C_{18}$alkyl such as methyl or $C_{17}$alkyl, or is $SO_3Na$; or
e is 4 and $G_3$ is a carbon atom;
or each of b, c and d is 0, e is 2 and $G_3$ is methylene or ethylidene.

Most preferred compounds are those of formula (1), especially wherein $G_1$ and $G_2$ are the tert-butyl radical; and a is 1.

It is also preferred to use compounds of formula

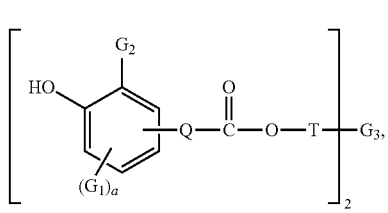

wherein
$G_1$ and $G_2$ are each independently of the other $C_1$-$C_5$alkyl;
Q is —$C_mH_{2m}$—; or —$C_mH_{2m}$—NH—;

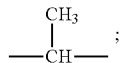

$G_3$ is a direct bond; —O—; —S—; —$CH_2$—; or
a is 1 or 2;
m is 1 to 5; and
T has the meaning cited in formula (1).

Interesting compounds of formula (1) are those, wherein
Q is ethylene; or

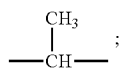

$G_3$ is a direct bond; and
$G_1$, $G_2$, T and a have the meanings given in formula (3).

Likewise preferred are compounds of formula

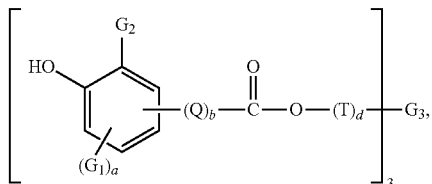

wherein
Q is —$C_mH_{2m}$—;
T is —$C_nH_{2n}$—;
$G_1$ and $G_2$ are each independently of the other $C_1$-$C_5$alkyl;
$G_3$ is the radical of formula (1g); (1h); (1i); or (1k);
m and n are each independently of the other 1 to 3;
a is 1 or 2; and
b and d are each independently of the other 0 or 1.

Other antioxidants which are preferably used conform to formula

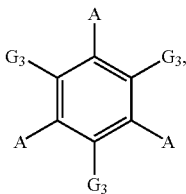

(5)

wherein
A is a radical of formula

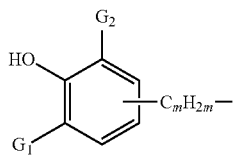

(5a)

$G_1$, $G_2$ and $G_3$ are each independently of one another $C_1$-$C_5$alkyl; and
m is 1 to 3.
Other preferred antioxidants are those of formula

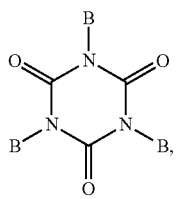

(6)

wherein
B is a radical of formula

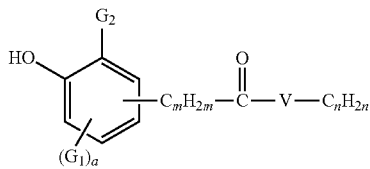

(6a)

$G_1$ and $G_2$ are each independently of the other $C_1$-$C_5$alkyl;
V is —O—; or —NH—;
a is 1; or 2;
m is 1 to 3; and
n is 0 to 3.

Present compounds, e.g. those of formulae (1), (2) and (3), previously have been known as antioxidants for plastics and certain other organic materials.

Within the present invention, they can be used as individual compounds or as mixtures of several individual compounds. Owing to their good solubility, they can be easily incorporated into the respective formulations.

Present compounds, e.g. those of formulae (1), (2), (3), can also be used together with tocopherol and/or tocopherol acetate, ascorbic acid and/or derivatives or esters thereof, retinal, retinal, retinoic acid and/or derivatives thereof.

Such further hydrophilic or lipophilic components are usually contained within the concentration range from 0.001% to 10% of the total weight of the preparation. Those additional components are preferably selected from the group consisting of tocopherol (α, β, γ, δ isomers) and its esters of acids with general formulas $$H(CH2)n(CHR)COOH \quad (1)$$

$$CH3(CH2)mCH=CH(CH2)nCOOH \quad (2)$$

where R is hydrogen atom or OH group, m, n are integral numbers from 0 to 22 where m+n sum is maximally 22;

tocotrienol (α, β, γ, δ isomers), containing one unsaturated fatty chain, and its esters of acids;

ascorbic acid and its esters of acids such as phosphoric acid and also sodium, potassium, lithium and magnesium salts, Ascorbyl Tetraisopalmitate, further ester with pyrrolidoncarboxylic acid and esters of acids with general formulas $$H(CH2)n(CHR)COOH \quad (3)$$

$$CH3(CH2)mCH=CH(CH2)nCOOH \quad (4)$$

where R is hydrogen atom or OH group, m, n are integral numbers from 0 to 20 where m+n sum is maximally 21;

retinoids including all natural and/or synthetic analogs of vitamin A or retinal-like compounds which possess the biological activity of vitamin A in the skin as well as the geometric isomers and stereoisomers of these compounds. Preferred compounds are retinal, retinol esters (e.g., $C_2$-$C_{22}$ alkyl esters (saturated or unsaturated alkyl chains) of retinal, including retinyl palmitate, retinyl acetate, retinyl propionate), retinal, and/or retinoic acid (including all trans retinoic acid and/or 13-cis-retinoic acid) or derivatives. Other retinoids which are useful herein are described in U.S. Pat. No. 4,677,120, issued Jun. 30, 1987 to Parish et al; U.S. Pat. No. 4,885,311, issued Dec. 5, 1989 to Parish et al; U.S. Pat. No. 5,049,584, issued Sep. 17, 1991 to Purcell et al., U.S. Pat. No. 5,124,356, issued Jun. 23, 1992 to Purcell et al. Other suitable retinoids are tocopheryl-retinoate [tocopherol ester of retinoic acid (trans or cis)], adapalene [6-(3-(1-adamantyl)-4-methoxyphenyl)-2-naphtoic acid] and tazarotene (ethyl 6-[2-(4,4-dimethylthiochroman-6-yl)-ethynyl]nicotinate);

carotenoids such as α-, β-, γ-, and δ-carotene, lutein, xanthophylls, zeaxanthine, violaxanthine, cryptoxanthine, fukoxanthine, antheraxanthine, lycopene, didehydrolycopene and tetradehydrolycopene carotenoids enzymatic antioxidants such as Glutathione peroxidase, Catalase, Superoxide dismutase;

Ubiquinone and Idebenone(hydroxydecyl Ubiquinone), Ubiquinol and its derivatives;

lipoic acid and its derivatives such as alpha-lipoic acid;

rutinic acid and its derivatives such as α-glucosylrutin, a water soluble flavonoid, rutin hydrate (vitamin P);

plant extracts such as white and green tea extracts, chicory leaf extract (*Cichorium intubybus*), Passionflower extract (*Passiflora incarnata*), *Aspalathus linearis* extract, rosmary extract, red leaf extract of Aceraceae Maple tree or of Rosaceae Cherry tree, *Curcuma longa* L (curcuminoids active ingredients), *Leontopodium alpinum* extract, *Emblica officinalis* (*phyllanthus emblica*) tree extract;

phenolic acids such as caffeic acid, 3,4-dihydroxyphenyl acetic acid, 3,4-dihydroxybenzoic acid;

flavonoids and polyphenols such as flavanones selected from the group consisting of unsubstituted flavanones, mono-substituted flavanones, and mixtures thereof; chalcones selected from the group consisting of unsubstituted Chalcones, mon-substituted chalcones, di-substituted chalcones, tri-substituted chalcones, and mixture thereof; flavones selected from the group consisting of unsubstituted flavones, mono-substituted flavones, di-substituted flavones, and mixtures thereof; one or more isoflavones; coumarins selected from the group consisting of unsubstituted coumarins, mono-substituted coumarins, di-substituted coumarins, and mixtures thereof; flavonols, anthocyanins, catechins, proanthocyanidins (Grape seed extract). Flavonoids which are broadly disclosed in U.S. Pat. Nos. 5,686,082 and 5,686,367 can also be used;

chlorogenic acid and ferulic acid.

It is also possible to use a further kind of antioxidant that interrupts the photochemical reaction chain triggered when UV radiation penetrates the skin or hair. Typical examples of such antioxidants are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotinoids, carotenes, lycopene and derivatives thereof, chlorogenic acid and derivatives thereof, lipoic acid and derivatives thereof (e.g. dihydrolipoic acid), aurothioglycose, propylthiouracil and other thiols (e.g. thioredoxin, glutathione, cysteine, cystine, cystamine and the glycosyl, N-acetyl, methyl, ethyl, propyl, amyl, butyl, lauryl, palmitoyl, oleyl, linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts) and also sulfoximine compounds (e.g. buthionine sulfoximines, homocysteine sulfoximine, buthionine sulfones, penta-, hexa-, hepta-thionine sulfoximine), also (metal) chelating agents (e.g. hydroxy fatty acids, palmitic acid phytic acid, lactoferrin, chitosan and derivatives such as phosphonomethylated chitosan) and preferably those disclosed in U.S. Pat. No. 5,487,884; WO91/16035; WO91/16034; hydroxy acids (e.g. citric acid, lactic acid, malic acid), humic acid, bile acid, bile extracts, bilirubin, biliverdin, EDTA, EDDS, EGTA and derivatives thereof, unsaturated fatty acids and derivatives thereof (e.g. linolenic acid, linoleic acid, oleic acid), folic acid and derivatives thereof, ubiquinone and ubiquinol and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate) and also coniferyl benzoate of benzoin resin, rutinic acid and derivatives thereof, glycosylrutin, ferulic acid, furfurylidene glucitol, carnosine, butyl hydroxytoluene, butyl hydroxyanisole, nordihydroguaiaretic acid, trihydroxybutyrophenone, uric acid and derivatives thereof, mannose and derivatives thereof, superoxide dismutase, N-[3-(3,5-di-tert-butyl-4-hydroxyphenyl)propionyl]sulfanilic acid (and salts thereof, for example the disodium salts), zinc and derivatives thereof (e.g. ZnO, ZnSO$_4$), selenium and derivatives thereof (e.g. selenium methionine), stilbene and derivatives thereof (e.g. stilbene oxide, trans-stilbene oxide) and the derivatives suitable according to the invention (salts, esters, ethers, sugars, nucleotides, nucleosides, peptides and lipids) of those mentioned active ingredients. Further HALS ("Hindered Amine Light Stabilizers") compounds may also be mentioned.

Further synthetic and natural antioxidants are listed e.g. in WO 00/25731 (see e.g. structures 1-3 (page 2), structure 4 (page 6), structures 5-6 (page 7) and compounds 7-33 (page 8-14)).

The topical application may additionally contain at least one further component with anti-inflammatory effect, preferably from 0.01% to 10% more preferably about 0.5% to about 5%, of the composition, such as:

steroidal anti-inflammatory agents, including but not limited to, corticosteroids such as hydrocortisone and their derivatives;

non-steroidal anti-inflammatory agents, including but not limited to, oxicams, salycilates, acetic acid derivatives, fenamates, propionic acid derivatives, pyrazoles;

natural anti-inflammatory agents including, but not limited to, α-bisabolol, allantoin, lyophilized extract of aloe vera, panthenol, betulin, compounds of the Licorice (*Glycyrrhiza glabra*) including glycyrrhetic acid, glycyrrhizic acid, and derivatives thereof (salts and esters) suc as sodium glycyrrhizinate, potassium glycyrrhizinate, ammonium glycyrrhizinate; botulinic acid, alkaline salts thereof and salts of alkaline-earth metals, boswellic acid, alkaline salts thereof and salts of alkaline-earth metals, rosemaric acid, alkaline salts thereof and salts of alkaline-earth metals; polynonsaturated fatty acids, as linoleic (18:2n6), α-linolenic (18:3n3), γ-linolenic (18:3n6), octadekanetetraenic (18:4n3), dihomo-γ-linolenic (20:3n6), eikosantetraenic (20:4n3), arachidonic (20:4n6), eikosanpentaenic (20:5n3) acids and esters thereof with alcohols of the general formula

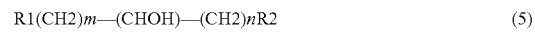

$$R1(CH2)m—(CHOH)—(CH2)nR2 \quad (5)$$

where R1 and R2 are hydrogen atoms or OH group, m, n are integral numbers from 0 to 17 where m+n sum is maximally 21;

phytosterols and their polyethoxylate derivatives of the general formulas (6) and (7) below, where R is isoalkyl or isoalkenyl group with 8-10 carbon atoms, where n is integral number from 0 to 50, especially campesterol, β-sitosterol, stigmasterol, cholesterol, Δ-5-avenasterol, Δ-7-avenasterol, brassicasterol, spinasterol and fukosterol

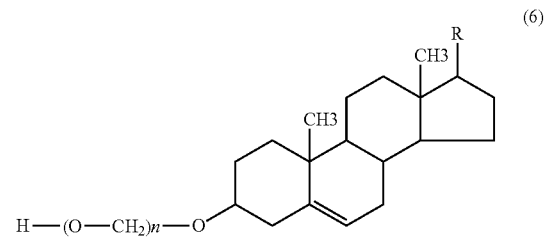

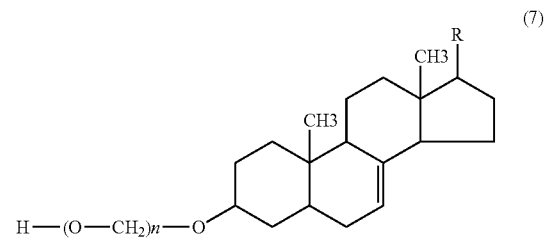

The pharmaceutical compositions include liquid, semisolid or solid preparations.

Examples of liquid pharmaceutical compositions are injectable solutions, infusion solutions, drops, sprays, aerosols, emulsions, lotions, suspensions, drinking solutions, gargles and inhalants.

Examples of semisolid pharmaceutical compositions are ointments, creams (O/W emulsions), rich creams (W/O emulsions), gels, lotions, foams, pastes, suspensions, ovula, plasters, including applications for transdermal systems such as masks, compresses, pads.

Examples of solid pharmaceutical compositions are tablets, coated tablets, capsules, granules, effervescent granules, effervescent tablets, lozenges, sucking and chewing tablets, suppositories, implants, lyophilisates, adsorbates or powders.

Preferred are liquid or semisolid preparations.

Galenic pharmaceutical compositions comprising the present compounds will be understood as meaning in particular emulsions, ointments, gels, sprays and powders; for example creams, gels, lotions, alcoholic and aqueous/alcoholic solutions, emulsions, wax/fat compositions, stick preparations such as lip sticks or deodorants, powders or ointments.

The final formulations listed may exist in a wide variety of presentation forms, for example:
in the form of liquid preparations as a W/O, O/W, O/W/O, W/O/W or PIT emulsion and all kinds of microemulsions,
in the form of a gel,
in the form of an oil, a cream, milk or lotion,
in the form of a powder, a lacquer, a tablet or make-up,
in the form of a stick,
in the form of a spray (spray with propellant gas or pump-action spray) or an aerosol,
in the form of a foam, or
in the form of a paste.

Several particulate skin care delivery systems are proposed:

A] Nanoemulsions and nanoparticles are mainly based on lecithin or fractionated phospholipids, especially
nanoemulsions with particle size range of 20 nm-50 nm represented by a single layer membrane, including Nanotopes (lipid core surrounded by a membrane composed of phospholipids and co-surfactants; stable and small size particle (smaller than liposomes) due to the intecalation of co-surfactant between the extending lecithin molecules) and Nanosomes;
nanoparticles with particle size range of 100 nm-300 nm represented by a bi-layer membrane;
Liposomes, i.e. spherical vesicles comprising amphiphilic lipids (predominantly phospholipids) enclosing an aqueous core and forming one or several concentric bi-layers; small unilamellar vesicles (SUV), large unilamellar vesicles (LUV), large multilamellar vesicles (MLV) or multivesicullar vesicles (MVV)).

The compounds of the invention may, for example, be incorporated into the bi-layers, into the aqueous core or distributed in both.

B] Microcapsules with particle size >1 μm based on matrix or encapsulation layer (spherical system based on a core material containing the active; the core is, then, surrounded by one or several coating layers or shells).

Polymers used to form those microcapsules include natural gums, cellulosic ingredients, polysaccharides, synthetic polyacrylates or polyacrylamides, polyvinyl alcohol (PVA), lipids, inorganics (silicates/clays), high molecular weight proteins such as gelatin, albumin etc.; examples include Nylon micro-porous spheres (Orgasol range from Elf Atochem), Mineral fillers such as sericite surface-treated by bi-functional coating (reaction between reactive fatty acid derivatives and the aqueous solution of sericite); Glycospheres (core based on modified starch and outer lipid membrane based on fatty acids and polar lipids); carbon nanotubes; Silica shells, made of silicates, for non aqueous and solid end-products such as sticks, dry powders etc.

C] Matrix particulate systems which entrap the active ingredient within the uniform core matrix; examples:
Solid Lipid Nanoparticle (SLN) technology based only on solid lipids;
Nanostructured Lipid Carriers (NLC) made of blend of solid lipid and liquid lipid (typical particle size diameter within the range 80 nm-1 μm);
Nanospheres (e.g. U.S. Pat. No. 6,491,902) represented by solid hydrophobic and highly cationic nanospheres (typical particle size range 10 nm to 1 μm) and based on solid hydrophobic matrix coated with highly cationic or bioadhesive layer.

D] Multi-walled delivery systems, e.g. systems similar to liposome structures but made only of non-phospholipidic "membrane-mimetic" amphiphiles such as oleic acid, saturated or unsaturated fatty acids, long-chain soaps combined with non ionic surfactants, derivatives of polyglycerol, di-ammonium amphiphiles, cationic surfactants, cationic amphiphiles involving amino acid residues, sucrose fatty acid esters, aqueous mixture of anionic and cationic surfactants.

E] Microsponge technology such as a system based on microscopic polymer-based sphere that consist of interconnecting voids within a non collapsible structure (non continuous shell); examples include a copolymer of styrene and divinylbenzene, or vinyl derivatives, water-swellable particles made of lactose, cellulose and cellulose derivatives such as Unispheres from Induchem etc.

F] Silicone-based vesicles such as multi-layers vesicles similar to liposome structures, where layers are made of polyether-modified dimethicone (dimethicone copolyol), silicone elastomers, blends of dimethicone crosspolymer, dimethicone/vinyldimethicone crosspolymer or PEG-modified dimethicone crosspolymer etc.

G] Cyclodextrins, usually oligomeric and cyclic carbohydrate compounds containing 6 to 8 glucose units such as α-, β- and γ-cyclodextrin.

According to a preferred method, the present compounds are applied in nanodispersed or encapsulated form such as described in US-2005-0191330 (see especially sections [0007-0079], [0120-0133] and examples) and US-2003-0190347 (see especially sections [0005-0087] and examples).

A further aspect of technical importance within the present invention is the finding that the present compounds are able to protect other active ingredients, especially oxidizable natural substances or active ingredients such as vitamins, plant extracts, fragrances etc., most effectively from premature degradation when encapsulated together with the ingredient. The present compounds in such cases thus are also useful in purely cosmetic formulations, where none of their pharmacological advantages are required, but the protection of another active, e.g. a vitamin such as vitamin A, E or C is sought.

Examples for end formulations containing the composition of the invention also include
skin-care preparations, e.g. skin-washing and cleansing preparations in the form of tablet-form or liquid soaps, soapless detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils;

personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and antiperspirants or callus-removing preparations;

light-protective preparations, such as sun milks, lotions, creams or oils, sunblocks or tropicals, pre-tanning preparations or after-sun preparations;

skin-tanning preparations, e.g. self-tanning creams;

depigmenting preparations, e.g. preparations for bleaching the skin or skin-lightening preparations including rinse off preparations such as soaps and leave on preparations such as creams etc.;

medicated bar soaps and liquid containing antifungals, anti bacterials etc.;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or perfume creams;

hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

Of special importance as preparations for the skin are daily care and/or anti-aging preparations, including light-protective preparations, such as sun milks, lotions, creams, oils, sunblocks or topicals, pretanning preparations or after-sun preparations, also skin-tanning preparations, for example self-tanning creams, skin whitener preparations, skin lightener preparations or combinations of such systems. Of particular interest are anti-aging preparations in combination with UV-protecting systems such as daily care creams, daily care lotions, daily care milk and daily care preparations in the form of a spray.

The compositions/preparations according to the invention may, where appropriate, also contain one or one more additional compounds as described below, especially in preparations for skin treatment:

Fatty Alcohols

Guerbet alcohols based on fatty alcohols having from 6 to 18, preferably from 8 to 10 carbon atoms including cetyl alcohol, stearyl alcohol, cetearyl alcohol, oleyl alcohol, octyldodecanol, benzoate of $C_{12}$-$C_{15}$ alcohols, acetylated lanolin alcohol, etc.

Esters of Fatty Acids

Esters of linear $C_6$-$C_{24}$ fatty acids with linear $C_3$-$C_{24}$ alcohols, esters of branched $C_6$-$C_{13}$carboxylic acids with linear $C_6$-$C_{24}$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer triol) and/or Guerbet alcohols, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerisation of unsaturated fatty acids) with alcohols, for example, isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerisation of unsaturated fatty alcohols).

Examples of such ester oils are isopropylmyristate, isopropylpalmitate, isopropylstearate, isopropyl isostearate, isopropyloleate, n-butylstearate, n-hexyllaurate, n-decyloleate, isooctylstearate, iso-nonylstearate, isononyl isononanoate, 2-ethylhexylpalmitate, 2-hexyllaurate, 2-hexyldecylstearate, 2-octyldodecylpalmitate, oleyloleate, oleylerucate, erucyloleate, erucylerucate, cetearyl octanoate, cetyl palmitate, cetyl stearate, cetyl oleate, cetyl behenate, cetyl acetate, myristyl myristate, myristyl behenate, myristyl oleate, myristyl stearate, myristyl palmitate, myristyl lactate, propylene glycol dicaprylate/caprate, stearyl heptanoate, diisostearyl malate, octyl hydroxystearate, etc.

Other Adjuvants alpha glucosylrutin (CAS No. 130603-71-3), 2-butyloctyl o-hydroxybenzoate (CAS No. 190085-41-7), vitamin E (CAS No. 1406-18-4), vitamin E acetate (CAS No. 58-95-7), diethylhexyl 2,6-naphthalate, di-n-butyl adipate, di(2-ethylhexyl)-adipate, di(2-ethylhexyl)-succinate and diisotridecyl acelaat, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate. Esters of $C_6$-$C_{24}$ fatty alcohols and/or Guerbet alcohols with aromatic carboxylic acids, saturated and/or unsaturated, especially benzoic acid, esters of $C_2$-$C_{12}$dicarboxylic acids with linear or branched alcohols having from 1 to 22 carbon atoms or polyols having from 2 to 10 carbon atoms and from 2 to 6 hydroxy groups, or iminodisuccinic acid and imiondisuccinic acid salts [CAS 7408-20-0] or latex particles, aloe vera, chamomile, ginko biloba, ginseng, coenzyme Q10, *laminaria ochroleuca* extract, *magnolia oborata* extract, *melalenca alternifolia* leaf oil, *rubus idaeus* seed oil, *vaccinium macrocarpon* seed oil, pumpkin seed extract, pumpkin seed oil, grape seed extract, carnosine, alpha-arbutin, madecassoside, terminolaside, tetrahydrocurcuminoids (THC), mycosporines, mycosporine like amino acids from the red alga *porphyra umbilicalis*, mycosporine-like amino acids (as described in WO2002039974), cis-9-octadecenedioic acid, lipoic acid, laurimino dipropiomic acid tocopheryl phosphates (LDTP), microcrystalline cellulose (MCC), polycarbonates as described in WO 0341676, sterols (cholesterol, lanosterol, phytosterols), as described in WO0341675 and linear poly-alpha-glucans as described in U.S. Pat. No. 6,616,935

Natural or Synthetic Triglycerides Including Glyceryl Esters and Derivatives

Di- or tri-glycerides, based on $C_6$-$C_{18}$ fatty acids, modified by reaction with other alcohols (caprylic/capric triglyceride, wheat germ glycerides, etc.). Fatty acid esters of polyglycerin (polyglyceryl-n such as polyglyceryl-4 caprate, polyglyceryl-2 isostearate, etc. or castor oil, hydrogenated vegetable oil, sweet almond oil, wheat germ oil, sesame oil, hydrogenated cottonseed oil, coconut oil, avocado oil, corn oil, hydrogenated castor oil, shea butter, cocoa butter, soybean oil, mink oil, sunflower oil, safflower oil, *macadamia* nut oil, olive oil, hydrogenated tallow, apricot kernel oil, hazelnut oil, borago oil, etc.

Waxes including esters of long-chain acids and alcohols as well as compounds having wax-like properties, e.g., carnauba wax, beeswax (white or yellow), lanolin wax, candellila wax, ozokerite, japan wax, paraffin wax, microcrystalline wax, ceresin, cetearyl esters wax, synthetic beeswax, etc. Also, hydrophilic waxes as Cetearyl Alcohol or partial glycerides.

Pearlescent Waxes:

Ikylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially (aurone and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

Hydrocarbon Oils:

Mineral oil (light or heavy), petrolatum (yellow or white), microcrystalline wax, paraffinic and isoparaffinic compounds, hydrogenated isoparaffinic molecules as polydecenes and polybutene, hydrogenated polyisobutene, squalane, isohexadecane, isododecane and others from plant and animal kingdom.

Silicones or Siloxanes (Organosubstituted Polysiloxanes)

Dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Linear polysiloxanes, dimethicone (Dow Corning 200 fluid, Rhodia Mirasil DM), dimethiconol, cyclic silicone fluids, cyclopentasiloxanes volatiles (Dow Corning 345 fluid), phenyltrimethicone (Dow Corning 556 fluid). Also suitable are simethicones, which are mixtures of dimethicones having an average chain length of from 200 to 300 dimethylsiloxane units with hydrogenated silicates. A detailed survey by Todd et al. of suitable volatile silicones may in addition be found in Cosm. Toil. 91, 27 (1976).

The term "silicones" stands for any organosilicon polymer or oligomer having a linear or cyclic, branched or crosslinked structure, of variable molecular weight, and essentially is based on recurring structural units in which the silicone atoms are linked to each other by oxygen atoms (siloxane bond SiOSi), optionally substituted hydrocarbon radicals being directly linked via a carbon atom to the silicone atoms.

Examples include:

Cyclic siloxane polymers; Cyclomethicones of the general formula

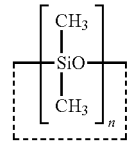

such as cyclopentasiloxane, cyclohexasiloxane (low viscous, volatile fluid; the INCI names for labeling specific cyclic dimethyl polysiloxane compounds are: Cyclotrisiloxane (q.v.) when n is equal to 3, Cyclotetrasiloxane (q.v.) when n is equal to 4, Cyclopentasiloxane (q.v.) when n is equal to 5, Cyclohexasiloxane (q.v.) when n is equal to 6, and Cycloheptasiloxane when n is equal to 7 (q.v.));

Linear siloxane polymer end-blocked with Trimethylsiloxy units (M unit) Dimethicones; non polar liquid with broad range of viscosity of the general formula

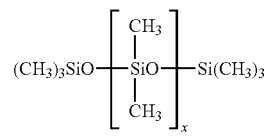

Silanol compounds or dimethiconols, such as Dimethyl siloxane terminated with hydroxyl groups (—OH) of the general formula

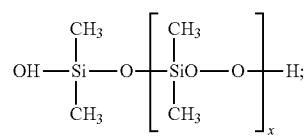

Silicone elastomers and resins obtained by crosslinking of siloxane structures such as Dimethicones (elastomer: medium crosslinking with a density that allows elongation/distortion of the molecule, usually excluding PEG-modified Dimethicone Crosspolymers; resin: high crosslinking with a density that provides some rigidity to the molecule).

Silicone elastomers useful as co-emulsifier systems include Dimethicone Crosspolymer in Cyclopentasiloxane (e.g. DC 9045 silicone elastomer blend by Dow Corning); Dimethicone Crosspolymer in Dimethicone (e.g. DC 9041 silicone elastomer blend by Dow Corning);

polymer of Dimethicone (q.v.) crosslinked with a $C_3$ to $C_{20}$ alkyl group; Dimethicone/Vinyldimethicone Crosspolymer (DC 9506 powder, Dow Corning); Dimethicone/Vinyldimethicone Crosspolymer in Cyclopentasiloxane (e.g. SFE 839 (GE silicones) or KSG 15 (Shin-Etsu));

copolymer of dimethylpolysiloxane crosslinked with vinyl dimethylpolysiloxane.

Resin silicones include dispersing agents such as KP-545 (Shin-Etsu);

Acrylates/Dimethicone copolymer in Cyclopentasiloxane; copolymer of dimethicone and one or more monomers of acrylic acid, methacrylic acid or one of their simple esters; Siloxysilicates such as Trimethylsiloxysilicates; T-resins; branched polymer of T-Units; Q-resins; branched polymer of Q-Units:

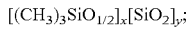

film-forming and water-resistant agents such as Trimethylsiloxysilicate (e.g. SR 399 (GE Silicones) or Wacker-Belsil TMS803 (Wacker Chemie), mixtures from Dow Corning such as DC 749 cosmetic fluid (Trimethylsiloxysilicate in Cyclopentasiloxane) or DC 593 fluid (Trimethylsiloxysilicate in Dimethicone));

alkyl-modified siloxanes (AMS), which improve spreadability and wash-off resistance or, e.g. for inorganic sunscreens, improve particle dispersion, reduce re-agglomeration, improve long-lasting effect on skin. Examples:

Alkyl Dimethicone of the general formula

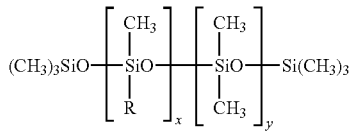

wherein R is —(CH2)n-CH3
such as bis-phenylpropyl Dimethicone (SF 1555 fluid; GE Silicone);
alkyl methicone of the general formula

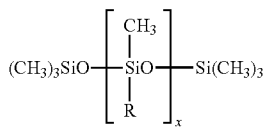

wherein R is —(CH2)n-CH3
i.e. silicone waxes such as DC 2503 cosmetic wax (Dow Corning); Stearyl Dimethicone DC 2502 fluid (Dow Corning); Cetyl Dimethicone; DC AMS-C30 wax (Dow Corning); 30-C45 Alkyl Methicone; DC 580 wax (Dow Corning); Stearoxytrimethylsilane and Stearyl Alcohol.

Fluorinated or Perfluorinated Oils

Perfluorhexane, dimethylcyclohexane, ethylcyclopentane, polyperfluoromethylisopropyl ether.

Emulsifiers

Any conventionally usable emulsifier can be used for the compositions. Emulsifier systems may comprise for example: carboxylic acids and their salts: alkaline soap of sodium, potassium and ammonium, metallic soap of calcium or magnesium, organic basis soap such as Lauric, palmitic, stearic and oleic acid etc. . . . . . Alkyl phosphates or phosphoric acid esters, acid phosphate, diethanolamine phosphate, potassium cetyl phosphate. Ethoxylated carboxylic acids or polyethyleneglycol esters, PEG-n acylates. Linear fatty alcohols having from 8 to 22 carbon atoms, branched from 2 to 30 mol of ethylene oxide and/or from 0 to 5 mol propylene oxide with fatty acids having from 12 to 22 carbon atoms and with alkylphenols having from 8 to 15 carbon atoms in the alkyl group. Fatty alcohol polyglycolether such as laureth-n, ceteareth-n, steareth-n, oleth-n. Fatty acid polyglycolether such as PEG-n stearate, PEG-n oleate, PEG-n cocoate. Monoglycerides and polyol esters. C12-C22 fatty acid mono- and di-esters of addition products of from 1 to 30 mol of ethylene oxide with polyols. Fatty acid and polyglycerol ester such as monostearate glycerol, diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable. Fatty acid polyglycolesters such as monostearate diethylene glycol, fatty acid and polyethylene glycol esters, fatty acid and saccharose esters such as sucro esters, glycerol and saccharose esters such as sucro glycerides. Sorbitol and sorbitan, sorbitan mono- and di-esters of saturated and unsaturated fatty acids having from 6 to 22 carbon atoms and ethylene oxide addition products.

Polysorbate-n series, sorbitan esters such as sesquiisostearate, sorbitan, PEG-(6)-isostearate sorbitan, PEG-(10)-sorbitan laurate, PEG-17-dioleate sorbitan. Glucose derivatives, C8-C22 alkyl-mono and oligo-glycosides and ethoxylated analogues with glucose being preferred as the sugar component. O/W emulsifiers such as methyl gluceth-20 sesquistearate, sorbitan stearate/sucrose cocoate, methyl glucose sesquistearate, cetearyl alcohol/cetearyl glucoside. W/O emulsifiers such as methyl glucose dioleate/methyl glucose isostearate. Sulfates and sulfonated derivatives, dialkylsulfosuccinates, dioctyl succinate, alkyl lauryl sulfonate, linear sulfonated parafins, sulfonated tetraproplyne sulfonate, sodium lauryl sulfates, ammonium and ethanolamine lauryl sulfates, lauryl ether sulfates, sodium laureth sulfates, sulfosuccinates, aceyl isothionates, alkanolamide sulfates, taurines, methyl taurines, imidazole sulfates. Amine derivatives, amine salts, ethoxylated amines, oxide amine with chains containing an heterocycle such as alkyl imidazolines, pyridine derivatives, isoquinoteines, cetyl pyridinium chlorure, cetyl pyridinium bromide, quaternary ammonium such as cetyltrimethylbroide ammonium broide (CTBA), stearylalkonium. Amide derivatives, alkanolamides such as acylamide DEA, ethoxylated amides such as PEG-n acylamide, oxydeamide. Polysiloxane/polyalkyl/polyether copolymers and derivatives, dimethicone, copolyols, silicone polyethylene oxide copolymer, silicone glycol copolymer. Propoxylated or POE-n ethers (Meroxapols), Polaxamers or poly(oxyethylene)m-block-poly(oxypropylene)n-block(oxyethylene). Zwitterionic surfactants that carry at least one quaternary ammonium group and at least one carboxylate and/or sulfonate group in the molecule. Zwitterionic surfactants that are especially suitable are betaines, such as N-alkyl-N,N-dimethylammonium glycinates, cocoalkyldimethylammonium glycinate, N-acylaminopropyl-N,N-dimethylammonium glycinates, cocoacylaminopropyldimethylammonium glycinate and 2-alkyl-3-carboxymethyl-3-hydroxyethylimidazolines each having from 8 to 18 carbon atoms in the alkyl or acyl group and also cocoacylaminoethylhydroxyethylcarboxymethylglycinate, N-alkylbetaine, N-alkylaminobetaines. Alkylimidazolines, alkylopeptides, lipoaminoacides, self emulsifying bases and the compounds as described in K. F. DePolo, A short textbook of cosmetology, Chapter 8, Table 8-7, p 250-251.

Non ionic emulsifiers such as PEG-6 beeswax (and) PEG-6 stearate (and) polyglyceryl-2-isostearate [Apifac], glyceryl stearate (and) PEG-100 stearate. [Arlacel 165], PEG-5 glyceryl stearate [arlatone 983 S], sorbitan oleate (and) polyglyceryl-3 ricinoleate. [Arlacel 1689], sorbitan stearate and sucrose cocoate [arlatone 2121], glyceryl stearate and laureth-23 [Cerasynth 945], cetearyl alcohol and ceteth-20 [Cetomacrogol Wax], cetearyl alcohol and colysorbate 60 and PEG-150 and stearate-20 [Polawax GP 200, Polawax NF], cetearyl alcohol and cetearyl polyglucoside [Emulgade PL 1618], cetearyl alcohol and ceteareth-20 [Emulgade 1000NI, Cosmowax], cetearyl alcohol and PEG-40 castor oil [Emulgade F Special], cetearyl alcohol and PEG-40 castor oil and sodium cetearyl sulfate [Emulgade F], stearyl alcohol and steareth-7 and steareth-10 [Emulgator E 2155], cetearyl alcohol and szeareth-7 and steareth-10 [Emulsifying wax U.S.N.F], glyceryl stearate and PEG-75 stearate [Gelot 64], propylene glycol ceteth-3 acetate. [Hetester PCS], propylene glycol isoceth-3 acetate [Hetester PHA], cetearyl alcohol and ceteth-12 and oleth-12 [Lanbritol Wax N 21], PEG-6 stearate and PEG-32 stearate [Tefose 1500], PEG-6 stearate and ceteth-20 and steareth-20 [Tefose 2000], PEG-6 stearate and ceteth-20 and glyceryl stearate and steareth-20 [Tefose 2561], glyceryl stearate and ceteareth-20 [Teginacid H, C, X].

Anionic emulsifiers such as PEG-2 stearate SE, glyceryl stearate SE [Monelgine, Cutina KD], propylene glycol stearate [Tegin P], cetearyl Alcohol and Sodium cetearyl sulfate [Lanette N, Cutina LE, Crodacol GP], cetearyl alcohol and sodium lauryl sulfate [Lanette W], trilaneth-4 phopshate and glycol stearate and PEG-2 stearate [Sedefos 75], glyceryl stearate and sodium lauryl Sulfate [Teginacid Special]. Cationic acid bases such as cetearyl alcohol and cetrimonium bromide.

Silicone emulsifiers particularly suitable for W/Si emulsions are those corresponding to the following formula:

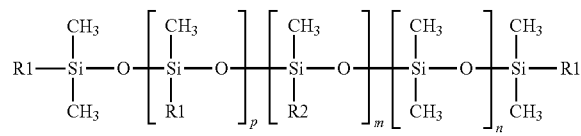

wherein
m is a number from 1 to 20
n is a number from 0 to 500
p is a number from 0 to 50
R1 is linear or branched C1-C30 Alkyl radical or phenyl radical
R2 is $-C_cH2_c-(-O-C2H4)_a-(-O-C3H6)_b-(-O-C4H8)_d-R3$
R3 is —H, —OH; linear or branched alkyl C1-C12; linear or branched alkoxy C1-C6; linear or branched acyloxy C2-C12; —NHCH2CH2COOM; aminoalkyl radical optionally substituted on the amine function; —NHCO(CH2)$_d$-COOM, C1-C30 carboxyacyl radical;
where M is H, Na, K, Li, NH4 or organic amine; optionally substituted phosphono group; —NHCO(CH2)$_d$OH; —NH3Y where Y is a monovalent organic or inorganic anion such as Cl, Br, Sulfate, Carboxylate (Acetate, Lactate, Citrate).
a is a number from 0 to 100
b is a number from 0 to 50; and
c is a number from 0 to 5
d is a number from 0 to 10.

These compounds represent the oxyalkylenated organo-modified silicones. Other denominations used are PEG/PPG Dimethicones (Dimethicone copolyols) or Silicone polyethers that clearly show surface active properties necessary to emulsify.

Preferred silicone emulsifiers which are particularly recommended correspond to formula

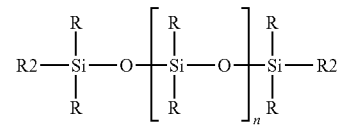

wherein
n is a number from 1 to 500
R is linear or branched $C_1$-$C_{30}$ Alkyl radical or phenyl radical
R2 is $-C_cH2_c-(-O-C2H4)_a-(-O-C3H6)_b-O(-C4H8)_d-R3$
R3, a, b, c & d have the same meaning as previously described A non exhaustive list of W/Si emulsifiers is given in the following table:

| INCI denomination |
|---|
| Oxyalkylenated organo-modified slicones: |
| PEG/PPG Dimethicones & Silicone polyethers |
| Bis-PEG/PPG -14/14 Dimethicone |
| Bis-PEG/PPG -20/20 Dimethicone |
| Bis-PEG/PPG -16/16 PEG/PPG -16/16Dimethicone |
| Bis_PEG-15 Methyl Ether Dimethicone |
| Bis(PPG-7 Undeceneth-21) Dimethicone |
| Cetyl PEG/PPG - 15/15 Butyl Ether Dimethicone |
| Cetyl PEG/PPG - 7/3 Dimethicone |
| Cetyl PEG/PPG - 10/1 Dimethicone |
| Dimethicone Copolyol |
| Dimethicone PEG-8 Adipate |
| Dimethicone PEG-7 Avocadoate |
| Dimethicone PEG-8 Avocadoate |
| Dimethicone PEG-8 Beeswax |
| Dimethicone PEG-n esters . . . |
| Dimethicone/PEG-10 Crosspolymer |
| Dimethicone/PEG-15 Crosspolymer |
| Dimethicone/PEG-7 Phosphate |
| Dimethicone/PEG-n Phosphates . . . |
| Dimethicone PEG/PPG-7/4 Phosphate |
| Dimethicone PEG/PPG-12/4 Phosphate |
| Dimethicone PEG-7 Undecylenate |
| Laurylmethicone copolyol |
| PEG-10 Dimethicone crosspolymer |
| PEG-12 Dimethicone crosspolymer |
| PEG-10 Lauryl Dimethicone Crosspolymer |
| PEG-15 Lauryl Dimethicone Crosspolymer |
| PEG-6 Methyl ether Dimethicone |
| PEG-n Methyl ether Dimethicones . . . |
| PEG-32 Methyl ether Dimethicone |

| INCI denomination |
|---|
| PEG/PPG - 20/22 Butyl Ether Dimethicone |
| PEG/PPG - 22/22 Butyl Ether Dimethicone |
| PEG/PPG - 23/23 Butyl Ether Dimethicone |
| PEG/PPG - 24/18 Butyl Ether Dimethicone |
| PEG/PPG - 27/9 Butyl Ether Dimethicone |
| PEG/PPG -3/10 Dimethicone |
| PEG/PPG - 5/3 Trisiloxane |
| PEG/PPG -n/m Dimethicones . . . |
| PEG/PPG -30/10 Dimethicone |
| Potassium Dimethicone PEG-7 Phosphate |
| PPG-12 Butyl Ether Dimethicone |
| PPG-12 Dimethicone |
| PPG-27 Dimethicone |
| TEA-Dimethicone PEG-7 Phosphate |
| Caprylyl Dimethicone Ethoxy Glucoside |
| Dimethicone Ethoxy Glucoside |
| Dimethicone/Polyglycerin-3 Crosspolymer |
| PEG-9 Polydimethylsiloxyethyl Dimethicone |
| Polydimethylsiloxy PEG/PPG - 24/19 Butyl Ether Silsesquioxane |
| Polydimethylsiloxy PPG-13 Butyl Ether Silsesquioxane |
| Polyglyceryl-3 Disiloxane Dimethicone |
| Polyglyceryl-3 Polydimethylsiloxyethyl Dimethicone |
| Sodium Carboxydecyl PEG-8 Dimethicone |
| Non-oxyalkylenated organo-modified silicones: |
| C6-8 Alkyl C3-6 Alkyl Glucoside Dimethicone |

The emulsifiers may be used in an amount of, for example, from 1 to 30% by weight, especially from 4 to 20% by weight and preferably from 5 to 10% by weight, based on the total weight of the composition.

When formulated in O/W emulsions, the preferably amount of such emulsifier system could represent 5% to 20% of the oil phase.

Adjuvants and Additives

Cosmetic/pharmaceutical preparations, for example creams, gels, lotions, alcoholic and aqueous/alcoholic solutions, emulsions, wax/fat compositions, stick preparations, powders or ointments, may in addition contain, as further adjuvants and additives, mild surfactants, super-fatting agents, consistency regulators, thickeners, polymers, stabilisers, biogenic active ingredients, deodorising active ingredients, anti-dandruff agents, film formers, swelling agents, further UV light-protective factors, antioxidants, hydrotropic agents, preservatives, insect repellents, self-tanning agents, solubilisers, perfume oils, colourants, bacteria-inhibiting agents and the like.

Super-Fatting Agents

Substances suitable for use as super-fatting agents are, for example, lanolin and lecithin and also polyethoxylated or acrylated lanolin and lecithin derivatives, polyol fatty acid esters, monoglycerides and fatty acid alkanolamides, the latter simultaneously acting as foam stabilisers.

Anti-Wrinkle Actives

The composition of the present preparation may further comprise suitable anti-wrinkle agents including sulfur-containing D and L amino acids and their derivatives and salts, particularly the N-acetyl derivatives, a preferred example of which is N-acetyl-L-cyteine; thiols; hydroxy acids (salicylic acid, glycolic acid), keto acids (pyruvic acid), phytic acid, lipoic acid; lysophophatidic acid, skin peel agents, flavonoids, stilbenes, cinnamates, resveratrol, kijnetin, zeatin, dimethylaminoethanol, peptides from natural and synthetic sources, salts of sugar acids (Mn gluconate), terpene alcohols, vitamin B compounds such as vitamin B3, vitamin B1 (Thiamine), vitamin B2 (riboflavin), vitamin B5 (Pantothenic acid), vitamin Bt (carnitine), Vitamin B12 (cobalamine), vitamin B15 (pangamic acid or diisopropylamine dichloroacetate) and their derivatives salts. metalloprotein-ase-inhibitors, trace-elements and trace-element-complexes such as Cu, Zn, Mn Co, Mg, or Se containing peptides, Skin Lightening Agents The composition of the present preparation may further comprise suitable skin lightening ingredients including kojic acid, arbutin, tranexamic acid, ascorbic acid and derivatives thereof, e.g., magnesium ascorbyl phosphate or sodium ascorbyl phosphate or other salts of ascorbyl phosphate. Also those ingredient displayed in the PCT application N° US 95/07432, filed on Feb. 24, 1995 and PCT application N° US 95/02809, filed on Jan. 3, 1995.

Surfactants

Examples of suitable mild surfactants, that is to say surfactants especially well tolerated by the skin, include fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, α-olefin sulfonates, ethercarboxylic acids, alkyl oligoglucosides, fatty acid glucamides, alkylamidobetaines and/or protein fatty acid condensation products, the latter preferably being based on wheat proteins.

Consistency Regulators/Thickeners and Rheology Modifiers

Silicium dioxide, magnesium silicates, aluminium silicates, polysaccharides or derivatives thereof for example hyaluronic acid, xanthan gum, guar-guar, agar-agar, alginates, carraghenan, gellan, pectines, or modified cellulose such as hydroxycellulose, hydroxypropylmethylcellulose. In addition polyacrylates or homopolymer of reticulated acrylic acids and polyacrylamides, carbomer (carbopol types 980, 981, 1382, ETD 2001, ETD2020, Ultrez 10) or Salcare range such as Salcare SC80 (steareth-10 alkyl ether/acrylates copolymer), Salcare SC81 (acrylates copolymer), Salcare SC91 and Salcare AST (sodium acrylates copolymer/PPG-1 trideceth-6), sepigel 305 (polyacrylamide/laureth-7), Simulgel NS and Simulgel EG (hydroxyethyl acrylate/sodium acryloyldimethyl taurate copolymer), Stabilen 30 (acrylates/vinyl isodecanoate crosspolymer), Pemulen TR-1 (acrylates/010-30 alkyl acrylate crosspolymer), Luvigel EM (sodium acrylates copolymer), Aculyn 28 (acrylates/beheneth-25 methacrylate copolymer), etc.

Viscosity additives set up network structures throughout the base fluid, and exhibit the "yield value". Clay and polymer additives possess high yield values, and are therefore used to positively support suspension problems. Regarding particle suspension, the addition of such viscosity building agents will help to decrease the density difference between the particle and the fluid media surrounding, and therefore will lead to better resistance to the settling down of the particles.

Thickeners can be divided into at least 2 general categories: those that show the best performance in water, and those that show the best performance in oils. In addition, it is also possible to differentiate them according to their nature, for example synthetic polymers, natural polymers and their derivatives, mineral polymers etc., but also according to their ionic character such as anionic, cationic, nonionic or amphoteric.

TABLE 4a

Natural thickeners
Most of them are derived from the Polysaccharides category

| | |
|---|---|
| RM 1 | Cellulose gum such as cross-linked or not Sodium Carboxymethylcellulose . . . or even Cocodimonium Hydroxypropyloxyethyl Cellulose |
| RM 2 | Microcrystalline cellulose and Carboxymethyl Cellulose Sodium |
| RM 3 | Guar gum and derivatives (except hydroxypropyl-modified), -Biosacccharide gum-1 (Fucogel 1000 from Solabia), -Sclerotium Gum (Amigel from Alban Muller) or Scleroglucan (Tinocare GL from Ciba SC) |
| RM 4 | Galactoarabinan from Larch extract (Laracare A200) |
| RM 5 | Acaccia/Arabic Gum |
| RM 6 | Konjac mannan; linear chains of glucose and mannose units linked in ($\beta$-1,4) |
| RM 7 | Pectin polysaccharides; backbone of galacturonic acid and rhamnose with side chains as Rhamnogalacturonan I or Rhamnogalacturonan II |
| RM 8 | Xanthan Gum; ($\beta$-1,4) linked Glucose residues or Dehydroxanthan Gum (Amaze XT from National Starch) |
| RM 9 | Starch and derivatives: Potato starch modified (Structure Solanace from National Starch); Hydroxypropyl Starch Phosphate (Structure XL or ZEA from National Starch); Amylose and Amylopectin polymeric forms; Maltodextrins |
| RM 10 | Carrageenan from red algae as Sulfated linear polysaccharides |
| RM 11 | Alginic acid and alginates from brown algae; polymers of mannuronic acid and Guluronic acid |

TABLE 4b

Mineral thickeners
Most of them are derived from smectite clays and silica derivatives

| | |
|---|---|
| RM 12 | Aluminum Silicates or Bentonites or Montmorillonites such as Magnesium Aluminum Silicates (Veegum range from R. T. Vanderbilt) and Quaternized compounds such as Stearalkonium Bentonite |
| RM 13 | Magnesium Silicates or Hectorites such as Bentone Series (from Elementis Specialties) and Quaternized compounds such as Disteardimonium Hectorite (to disperse in lipophilic media) |
| RM 14 | Magnesium sodium Fluorosilicate or modified Mica |
| RM 15 | Synthetic layered Silicates; similar structure to Hectorites; Sodium Magnesium Silicates (Laponite range from Solvay) |
| RM 16 | Fumed Silicas such as Aerosil range from Degussa |

TABLE 4c

Synthetic Rheology modifiers
Poly(acrylic acid) PAA and its copolymers; within such structure, it can be incorporated ester groups, with hydrophilic character such as 2-Hydroxyethyl Methacrylate etc.

| | |
|---|---|
| RM 17 | Carbomer or crosslinked polyacrylic acid polymer such as Carbopol Ultrez 10, Carbopol ETD2001, Carbopol ETD2050 from Noveon Inc |
| RM 18 | Sodium polyacrylate (Cosmedia SP from Cognis), Acrylates copolymer (Carbopol Aqua SF-1 from Noveon Inc.), Acrylates/acrylamides Coplymer (Noveon EC-1 from Noveon Inc.) |
| RM 19 | Hydroxyethyl/Acrylate/Sodium Acryloyldimethyl Taurate copolymer (Simulgel NS or EG from Seppic); combination with Tinosorb M claimed in PCA N°161 November 2001 |
| RM 20 | Ammonium Polyacrylates (Simulgel A from Seppic) |
| | i.e."Hydro Swelling Droplets" concept |
| RM 21 | Glyceryl Polyacrylates (e.g., Hispagel 100) or Polymethacrylates (e.g., Lubrajel range from ISP Corp.) |
| RM 22 | Poly(Acrylamide) PAAm and its copolymers; copolymers of ammonium acrylate and acrylamide; copolymers of AAam with long hydrophobic chain and acrylates |
| RM 23 | Poly(Ethylene oxide) PEO and Poly (Propylene oxide) PPO and their copolymers; these are block terpolymers of EO and PO with the structure ABA or BAB; A: PEO with good water solubility B: PPO with limited water solubility |
| RM 24 | Poly(VinylPyrrolidone)PVP homopoplymers or Poly(VinylPyrrolidone)/Vinyl Acetate coplymers |
| RM 25 | Poly (vinylalcohol) PVA |
| RM 26 | VA/Crotonates copolymer Poly(vinylacetate)/Crotonic acid or VA/Crotonates/Vinyl Neodecanoate copolymer |
| RM 27 | Ethylene/VinylAcetate copolymer such as A.C.coplymer400 (Allied-Signal) |
| RM 28 | PVM/MA copolymers and their esterified derivatives such Ethyl, Isopropyl or Butyl esters |
| RM 29 | PVM/MA Decadiene Crosspolymer; copolymer of methyl vinyl ether/Maleic Anhydric (PVM/MA) crosslinked with 1,9-decadiene |
| RM 30 | Polyethylene resins such as PEG-2M to PEG-9M (RITA Corp.) |
| RM 31 | polysiloxanes and copolymers; copolymers of polysiloxanes and other blocks such as PEO blocks |
| RM 32 | PEG-modified materials, the most commonly used class of non ionic thickeners with the following basic structure: $R(OCH_2CH_2)_n$ OH, werein R is the fatty moiety, like fatty alcohol, glyceryl ester, propylene glycol ester or carboxylic |

TABLE 4c-continued

Synthetic Rheology modifiers
Poly(acrylic acid) PAA and its copolymers; within such structure, it can be incorporated
ester groups, with hydrophilic character such as 2-Hydroxyethyl Methacrylate etc.

| | acid; for example; PEG-150 Distearate; these thickeners are not susceptible to hydrolysis and offer better viscosity stability under a broad range of pH and temperature profiles |
|---|---|
| RM 33 | Trihydroxystearin or Glycol Tri-(12-Hydroxystearate) |
| RM 34 | Glyceryl Tribehenate such as Syncrowax HRS-C from Croda |

TABLE 4d

Phospholid derivatives

RM 35 Alkylated Phosphatidyl Choline forming fluid lamellar assembly as the stable liquid crystalline phase of general formula:

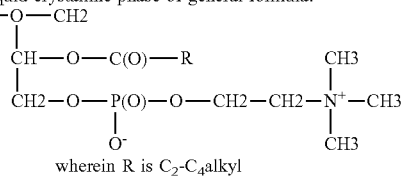

wherein R is $C_2$-$C_4$ alkyl

RM 36 Phosphobetaines (amphoteric ingredients); alkylamido Phosphobetaine of general formula

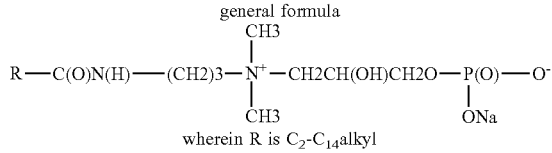

wherein R is $C_2$-$C_{14}$ alkyl

RM 37 Alkyl Phosphate Quaternary compounds of general formula

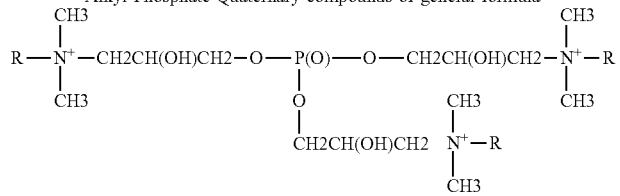

wherein R is $C_2$-$C_{14}$ alkyl

Polymers

Suitable cationic polymers are, for example, cationic cellulose derivatives, for example a quaternised hydroxymethyl cellulose obtainable under the name Polymer JR 400 from Amerchol, cationic starches, copolymers of diallylammonium salts and acrylamides, quarternised vinyl-pyrrolidone/vinyl imidazole polymers, for example Luviquat® (BASF), condensation products of polyglycols and amines, quaternised collagen polypeptides, for example lauryldimonium hydroxypropyl hydrolyzed collagen (Lamequa® L/Grünau), quaternised wheat polypeptides, polyethyleneimine, cationic silicone polymers, for example amidomethicones, copolymers of adipic acid and dimethylaminohydroxypropyldiethylenetriamine (Cartaretin/Sandoz), copolymers of acrylic acid with dimethyldiallylammonium chloride (Merquat 550/Chemviron), polyaminopolyamides, as described, for example, in FR-A-2 252 840, and the crosslinked water-soluble polymers thereof, cationic chitin derivatives, for example of quaternised chitosan, optionally distributed as microcrystals; condensation products of dihaloalkyls, for example dibromobutane, with bisdialkylamines, for example bisdimethylamino-1,3-propane, cationic guar gum, for example Jaguar C-17, Jaguar C-16 from Celanese, quaternised ammonium salt polymers, for example Mirapol A-15, Mirapol AD-1, Mirapol AZ-1 from Miranol. As anionic, zwitterionic, amphoteric and non-ionic polymers there come into consideration, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyl-trimethylammonium chloride/acrylate copolymers, octyl acrylamide/methyl methacrylatetert-butylaminoethyl methacrylate/2-hydroxypropyl methacrylate copolymers, polyvinylpyrrolidone, vinyl pyrrolidone/vinyl acetate copolymers, vinylpyrrolidone/dimethylaminoethyl methacrylate/vinyl caprolactam terpolymers and also optionally derivatised cellulose ethers and silicones. Furthermore the polymers as described in EP 1093796 (pages 3-8, paragraphs 17-68) may be used.

Biogenic Active Ingredients

Biogenic active ingredients are to be understood as meaning, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Deodorising Active Ingredients

As deodorising active ingredients there come into consideration, for example, antiperspirants, for example aluminium chlorohydrates (see J. Soc. Cosm. Chem. 24, 281 (1973)). Under the trade mark Locron® of Hoechst AG, Frankfurt (FRG), there is available commercially, for example, an aluminium chlorohydrate corresponding to formula $Al_2(OH)_5Cl \times 2.5H_2O$, the use of which is especially preferred (see J. Pharm. Pharmacol. 26, 531 (1975)). Besides the chlorohydrates, it is also possible to use aluminium hydroxyacetates and acidic aluminium/zirconium salts. Esterase inhibitors may be added as further deodorising active ingredients. Such inhibitors are preferably trialkyl citrates, such as trimethyl citrate, tripropyl citrate, triisopropyl citrate, tributyl citrate and especially triethyl citrate (Hydagen CAT, Henkel), which inhibit enzyme activity and hence reduce odour formation. Further substances that come into consideration as esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid or tartaric acid diethyl ester. Antibacterial active ingredients that influence the germ flora and kill or inhibit the growth of sweat-decomposing bacteria can likewise be present in the preparations (especially in stick preparations). Examples include chitosan, phenoxyethanol and chlorhexidine gluconate. 5-chloro-2-(2,4-dichlorophenoxy)-phenol (Triclosan, Irgasan, Ciba Specialty Chemicals Inc.) has also proved especially effective.

Anti-Dandruff Agents

As anti-dandruff agents there may be used, for example, climbazole, octopirox and zinc pyrithione. Customary film formers include, for example, chitosan, microcrystalline chitosan, quaternised chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds.

Hydrotropic Agents

To improve the flow behaviour it is also possible to employ hydrotropic agents, for example ethoxylated or non ethoxylated mono-alcohols, diols or polyols with a low number of carbon atoms or their ethers (e.g. ethanol, isopropanol, 1,2-dipropanediol, propyleneglycol, glyerin, ethylene glycol, ethylene glycol monoethylether, ethylene glycol monobutylether, propylene glycol monomethylether, propylene glycol monoethylether, propylene glycol monobutylether, diethylene glycol monomethylether; diethylene glycol monoethylether, diethylene glycol monobutylether and similar products). The polyols that come into consideration for that purpose have preferably from 2 to 15 carbon atoms and at least two hydroxy groups. The polyols may also contain further functional groups, especially amino groups, and/or may be modified with nitrogen. Typical examples are as follows: glycerol, alkylene glycols, for example ethylene glycol, diethylene glycol, propylene glycol, butylene glycol, hexylene glycol and also polyethylene glycols having an average molecular weight of from 100 to 1000 Dalton; technical oligoglycerol mixtures having an intrinsic degree of condensation of from 1.5 to 10, for example technical diglycerol mixtures having a diglycerol content of from 40 to 50% by weight; methylol compounds, such as, especially, trimethylolethane, trimethylolpropane, trimethylolbutane, pentaerythritol and dipentaerythritol; lower alkyl-glucosides, especially those having from 1 to 8 carbon atoms in the alkyl radical, for example methyl and butyl glucoside; sugar alcohols having from 5 to 12 carbon atoms, for example sorbitol or mannitol; sugars having from 5 to 12 carbon atoms, for example glucose or saccharose; amino sugars, for example glucamine; dialcohol amines, such as diethanolamine or 2-amino-1,3-propanediol.

Preservatives and Bacteria-Inhibiting Agents

Suitable preservatives include, for example, Methyl-, Ethyl-, Propyl-, Butyl-parabens, Benzalkonium chloride, 2-Bromo-2-nitro-propane-1,3-diol, Dehydroacetic acid, Diazolidinyl Urea, 2-Dichloro-benzyl alcohol, DMDM hydantoin, Formaldehyde solution, Methyldibromoglutanitrile, Phenoxyethanol, Sodium Hydroxymethylglycinate, Imidazolidinyl Urea, Triclosan and further substance classes listed in the following reference: K. F. DePolo—A short textbook of cosmetology, Chapter 7, Table 7-2, 7-3, 7-4 and 7-5, p 210-219. Typical examples of bacteria-inhibiting agents are preservatives that have a specific action against gram-positive bacteria, such as 2,4,4'-trichloro-2'-hydroxy-diphenyl ether, chlorhexidine (1,6-di(4-chlorophenyl-biguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorising agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% by weight, based on the solids content of the preparations.

Perfume Oils mixtures of natural and/or synthetic aromatic substances, for example, extracts from blossom (lilies, lavender, roses, jasmine, neroli, ylang-ylang), from stems and leaves (geranium, patchouli, petitgrain), from fruit (aniseed, coriander, carraway, juniper), from fruit peel (bergamot, lemons, oranges), from roots (mace, angelica, celery, cardamom, *costus*, iris, calmus), from wood (pinewood, sandalwood, guaiacum wood, cedarwood, rosewood), from herbs and grasses (tarragon, lemon grass, sage, thyme), from needles and twigs (spruce, pine, Scots pine, mountain pine), from resins and balsams (galbanum, elemi, benzoin, myrrh, olibanum, opoponax). Animal raw materials also come into consideration, for example civet and castoreum. Typical synthetic aromatic substances are, for example, products of the ester, ether, aldehyde, ketone, alcohol or hydrocarbon type. Aromatic substance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the ionones, isomethylionone and methyl cedryl ketone; the alcohols include, for example, anethol, citronellol, eugenol, isoeugenol, geraniol, linalool, phenyl ethyl alcohol and terpinol; and the hydrocarbons include mainly the terpenes and balsams. It is preferable, however, to use mixtures of various aromatic substances that together produce an attractive scent. Ethereal oils of relatively low volatility, which are chiefly used as aroma components, are also suitable as perfume oils, e.g. sage oil, camomile oil, clove oil, melissa oil, oil of cinnamon leaves, lime blossom oil, juniper berry oil, vetiver oil, olibanum oil, galbanum oil, labolanum oil and lavandin oil. Preference is given to the use of bergamot oil, dihydromyrcenol, lilial, lyral, citronellol, phenyl ethyl alcohol, hexyl cinnamaldehyde, geraniol, benzyl acetone, cyclamen aldehyde, linalool, boisambrene forte, ambroxan, indole, hedione, sandelice, lemon oil, tangerine oil, orange oil, allyl amyl glycolate, cyclovertal, lavandin oil, muscatel sage oil, damascone, bourbon geranium oil, cyclohexyl salicylate, vertofix coeur, iso-E-Super, Fixolide NP, evernyl, iraldein gamma, phenylacetic acid, geranyl acetate, benzyl acetate, rose oxide, romillat, irotyl and floramat alone or in admixture with one another.

Colourants

There may be used as colourants the substances that are suitable and permitted for cosmetic purposes, as compiled, for example, in the publication "Kosmetische Färbemittel" of the Farbstoffkommission der Deutschen Forschungsgemeinschaft, Verlag Chemie, Weinheim, 1984, pages 81 to 106. The colourants are usually used in concentrations of from 0.001 to 0.1% by weight, based on the total mixture.

Other Adjuvants

Anti-foams, such as silicones, structurants, such as maleic acid, solubilisers, such as ethylene glycol, propylene glycol, glycerol or diethylene glycol, opacifiers, such as latex, styrene/PVP or styrene/acrylamide copolymers, complexing agents, such as EDTA, NTA, alaninediacetic acid or phosphonic acids, propellants, such as propane/butane mixtures, $N_2O$, dimethyl ether, $CO_2$, $N_2$ or air, so-called coupler and developer components as oxidation dye precursors, reducing agents, such as thioglycolic acid and derivatives thereof, thiolactic acid, cysteamine, thiomalic acid or mercaptoethanesulfonic acid, or oxidising agents, such as hydrogen peroxide, potassium bromate or sodium bromate.

Suitable insect repellents are, for example, N,N-diethyl-m-toluamide, 1,2-pentanediol or insect repellent 3535; suitable self-tanning agents are, for example, dihydroxyacetone and/or erythrulose or dihydroxy acetone and/or dihydroxy acetone precursors as described in WO 01/85124 and/or erythrulose.

Polymeric beads or hollow spheres may be used as SPF enhancers.

Present compounds, e.g. those of formulae (1), (2) and/or (3), may also be contained in liposomes or used in pharmacological compositions with conventional carriers and penetration enhancers, for example urea, dextrane, propylene glycol, oleic acid and the like.

The pharmaceutical composition will usually contain the present compounds in amounts of 0.001 to 10% by weight, preferably of 0.01 to 5%, especially 0.01 to 2% by weight, of the total mixture. For the treatment of the conditions listed hereinabove, the pharmaceutical composition of this invention may contain, in addition to the present compounds, further pharmaceutical or cosmetic agents, e.g. having antiphlogistic activity, typically including antiinflammatory agents, vitamins, and/or, where appropriate, antipsoriatic agents, further skin actives, cell proliferation regulators, antiallergic, UV protecting, moisturizing, antiageing, gastroprotective, antiasthmatic agents, DNA-protectants.

The pharmaceutical composition of this invention may contain antioxidants and/or light stabilisers apart from present formulae (1)-(3), especially UV absorbers. Suitable components of these classes include those described in EP-A-955355, WO00/25730, WO00/25731, WO03/103622, EP-A-1366763.

Examples are components listed below:

Suitable UV filter substances which can be additionally used with the present compounds p-aminobenzoic acid derivatives, for example 4-dimethylaminobenzoic acid 2-ethylhexyl ester;
salicylic acid derivatives, for example salicylic acid 2-ethylhexyl ester;
benzophenone derivatives, for example 2-hydroxy-4-methoxybenzophenone and its 5-sulfonic acid derivative;
dibenzoylmethane derivatives, for example 1-(4-tert-butylphenyl)-3-(4-methoxyphenyl)-propane-1,3-dione;
diphenylacrylates, for example 2-ethylhexyl 2-cyano-3,3-diphenylacrylate, and 3-(benzofuranyl) 2-cyanoacrylate;
3-imidazol-4-ylacrylic acid and esters;
benzofuran derivatives, especially 2-(p-aminophenyl)benzofuran derivatives, described in EP-A-582 189, US-A-5 338 539, US-A-5 518 713 and EP-A-613 893;
polymeric UV absorbers, for example the benzylidene malonate derivatives described in EP-A-709 080;
cinnamic acid derivatives, for example the 4-methoxycinnamic acid 2-ethylhexyl ester and isoamyl ester or cinnamic acid derivatives described in US-A-5 601 811 and WO 97/00851;
camphor derivatives, for example 3-(4'-methyl)benzylidene-bornan-2-one, 3-benzylidene-bornan-2-one, N-[2(and 4)-2-oxyborn-3-ylidene-methyl)-benzyl]acrylamide polymer, 3-(4'-trimethylammonium)-benzylidene-bornan-2-one methyl sulfate, 3,3'-(1,4-phenylenedimethine)-bis(7,7-dimethyl-2-oxo-bicyclo[2.2.1]heptane-1-methanesulfonic acid) and salts, 3-(4'-sulfo)benzylidene-bornan-2-one and salts; camphorbenzalkonium methosulfate;
hydroxyphenyltriazine compounds, for example 2-(4'-methoxyphenyl)-4,6-bis(2'-hydroxy-4'-n-octyloxyphenyl)-1,3,5-triazine; 2,4-bis{[4-(3-(2-propyloxy)-2-hydroxy-propyloxy)-2-hydroxy]-phenyl}-6-(4-methoxyphenyl)-1,3,5-triazine; 2,4-bis{[4-(2-ethyl-hexyloxy)-2-hydroxy]-phenyl}-6-[4-(2-methoxyethyl-carboxyl)-phenylamino]-1,3,5-triazine; 2,4-bis{[4-(tris-(trimethylsilyloxy-silylpropyloxy)-2-hydroxy]-phenyl}-6-(4-methoxyphenyl)-1,3,5-triazine; 2,4-bis{[4-(2"-methylpropenyloxy)-2-hydroxy]-phenyl}-6-(4-methoxyphenyl)-1,3,5-triazine; 2,4-bis{[4-(1',1',1',3',5',5',5'-heptamethyltrisilyl-2"-methyl-propyloxy)-2-hydroxy]-phenyl}-6-(4-methoxyphenyl)-1,3,5-triazine; 2,4-bis{[4-(3-(2-propyloxy)-2-hydroxy-propyloxy)-2-hydroxy]-phenyl}-6-[4-ethylcarboxy)-phenylamino]-1,3,5-triazine;
benzotriazole compounds, for example 2,2'-methylene-bis(6-(2H-benzotriazol-2-yl)-4-(1,1,3,3-tetramethylbutyl)-phenol;
trianilino-s-triazine derivatives, for example 2,4,6-trianiline-(p-carbo-2'-ethyl-1'-oxy)-1,3,5-triazine and the UV absorbers disclosed in US-A-5 332 568, EP-A-517 104, EP-A-507 691, WO 93/17002 and EP-A-570 838;

| Suitable UV filter substances which can be additionally used with the present compounds |
|---|
| 2-phenylbenzimidazole-5-sulfonic acid and salts thereof;
menthyl o-aminobenzoates;
physical sunscreens coated or not as titanium dioxide, zinc oxide, iron oxides, mica, MnO, $Fe_2O_3$, $Ce_2O_3$, $Al_2O_3$, $ZrO_2$. (surface coatings: polymethylmethacrylate, methicone (methylhydrogenpolysiloxane as described in CAS 9004-73-3), dimethicone, isopropyl titanium triisostearate (as described in CAS 61417-49-0), metal soaps as magnesium stearate (as described in CAS 4086-70-8), perfluoroalcohol phosphate as C9-15 fluoroalcohol phosphate (as described in CAS 74499-44-8; JP 5-86984, JP 4-330007)). The primary particle size is an average of 15 nm-35 nm and the particle size in dispersion is in the range of 100 nm-300 nm.
aminohydroxy-benzophenone derivatives disclosed in DE 10011317, EP 1133980 and EP 1046391
phenyl-benzimidazole derivatives as disclosed in EP 1167358
the UV absorbers described in "Sunscreens", Eds. N. J. Lowe, N. A. Shaath, Marcel Dekker, Inc., New York and Basle or in Cosmetics & Toiletries (107), 50ff (1992) also can be used as additional UV protective substances. |

| No. | Chemical Name | CAS No. |
|---|---|---|
| 1 | (+/−)-1,7,7-trimethyl-3-[(4-methylphenyl)methylene]bicyclo[2.2.1]-heptan-2-one; p-methyl benzylidene camphor | 36861-47-9 |
| 2 | 1,7,7-trimethyl-3-(phenylmethylene)bicyclo[2.2.1]heptan-2-one; benzylidene camphor | 15087-24-8 |
| 3 | (2-Hydroxy-4-methoxyphenyl)(4-methylphenyl)methanone | 1641-17-4 |
| 4 | 2,4-dihydroxybenzophenone | 131-56-6 |
| 5 | 2,2',4,4'-tetrahydroxybenzophenone | 131-55-5 |
| 6 | 2-Hydroxy-4-methoxy benzophenone | 131-57-7 |
| 7 | 2-Hydroxy-4-methoxy benzophenone-5-sulfonic acid | 4065-45-6 |
| 8 | 2,2'-dihydroxy-4,4'-dimethoxybenzophenone | 131-54-4 |
| 9 | 2,2'-Dihydroxy-4-methoxybenzophenone | 131-53-3 |
| 10 | Alpha-(2-oxoborn-3-ylidene)toluene-4-sulphonic acid and its salts; Mexoryl SL | 56039-58-8 |
| 11 | 1-[4-(1,1-dimethylethyl)phenyl]-3-(4-methoxyphenyl)propane-1,3-dione; avobenzone | 70356-09-1 |
| 12 | Methyl N,N,N-trimethyl-4-[(4,7,7-trimethyl-3-oxobicyclo[2,2,1]hept-2-ylidene)methyl]anilinium sulphate; Mexoryl SO | 52793-97-2 |
| 22 | 3,3,5-Trimethyl cyclohexyl-2-hydroxy benzoate; homosalate | 118-56-9 |
| 23 | Isopentyl p-methoxycinnamate; isoamyl methoxy cinnamate | 71617-10-2 |
| 27 | Menthyl-o-aminobenzoate | 134-09-8 |
| 28 | Menthyl salicylate | 89-46-3 |
| 29 | 2-Ethylhexyl 2-cyano,3,3-diphenylacrylate; Octocrylene | 6197-30-4 |
| 30 | 2-ethylhexyl 4-(dimethylamino)benzoate | 21245-02-3 |
| 31 | 2-ethylhexyl 4-methoxycinnamate; octyl methoxy cinnamate | 5466-77-3 |
| 32 | 2-ethylhexyl salicylate | 118-60-5 |
| 33 | Benzoic acid, 4,4',4''-(1,3,5-triazine-2,4,6-triyltriimino)tris-, tris(2-ethylhexyl)ester; 2,4,6-Trianilino-(p-carbo-2'-ethylhexyl-1'-oxi)-1,3,5-triazine; octyl triazone | 88122-99-0 |
| 34 | 4-aminobenzoic acid | 150-13-0 |
| 35 | Benzoic acid, 4-amino-, ethyl ester, polymer with oxirane | 113010-52-9 |
| 38 | 2-phenyl-1H-benzimidazole-5-sulphonic acid; phenylbenzimidazolsulfonic acid | 27503-81-7 |
| 39 | 2-Propenamide, N-[[4-[(4,7,7-trimethyl-3-oxobicyclo[2.2.1]hept-2-ylidene)methyl]phenyl]methyl]-, homopolymer | 147897-12-9 |
| 40 | Triethanolamine salicylate | 2174-16-5 |
| 41 | 3,3'-(1,4-phenylenedimethylene)bis[7,7-dimethyl-2-oxo-bicyclo[2.2.1]heptane-1 methanesulfonic acid]; Cibafast H | 90457-82-2 |
| 42 | Titanium dioxide | 13463-67-7 |
| 44 | Zinc oxide | 1314-13-2 |
| 45 | 2,2'-Methylene-bis-[6-(2H-benzotriazol-2-yl)-4-(1,1,3,3-tetramethyl-butyl)-phenol]; Tinosorb M | 103597-45-1 |
| 46 | 2,4-bis{[4-(2-ethylhexyloxy)-2-hydroxy]-phenyl}-6-(4-methoxyphenyl)-(1,3,5)-triazine; Tinosorb S | 187393-00-6 |
| 47 | 1H-Benzimidazole-4,6-disulfonic acid, 2,2'-(1,4-phenylene)bis-, disodium salt | 180898-37-7 |
| 48 | Benzoic acid, 4,4'-[[6[[[(1,1-dimethylethyl)amino]carbonyl]phenyl]-amino]1,3,5-triazine-2,4-diyl]diimino]bis-, bis(2-ethylhexyl)ester; di-ethylhexyl butamido triazone; Uvasorb HEB | 154702-15-5 |
| 49 | Phenol, 2-(2H-benzotriazol-2-yl)-4-methyl-6-[2-methyl-3[1,3,3,3-tetramethyl-1-[(trimethylsilyl)oxy]disiloxanyl]propyl]-; drometrizole trisiloxane; Mexoryl XL | 155633-54-8 |
| 50 | Dimethicodiethylbenzalmalonate; Polysilicone 15; Parsol SLX | 207574-74-1 |
| 51 | Benzenesulfonic acid, 3-(2H-benzotriazol-2-yl)-4-hydroxy-5-(1-methylpropyl)-, monosodium salt ; Tinogard HS | 92484-48-5 |

| No. | Chemical Name | CAS No. |
|---|---|---|
| 52 | Benzoic acid, 2[4-(diethylamino)-2-hydroxybenzoyl]-, hexyl ester; Uvinul a plus | 302776-68-7 |
| 53 | 1-Dodecanaminium, N-[3-[[4-(dimethylamino)benzoyl]amino]propyl]-N,N-dimethyl-, salt with 4-methylbenzenesulfonic acid (1:1); Escalol HP610 | 156679-41-3 |
| 54 | 1-Propanaminium, N,N,N-trimethyl-3-[(1-oxo-3-phenyl-2-propenyl)-amino]-, chloride | 177190-98-6 |
| 55 | 1H-Benzimidazole-4,6-disulfonic acid, 2,2'-(1,4-phenylene)bis- | 170864-82-1 |
| 56 | 1,3,5-Triazine, 2,4,6-tris(4-methoxyphenyl)- | 7753-12-0 |
| 57 | 1,3,5-Triazine, 2,4,6-tris[4-[(2-ethylhexyl)oxy]phenyl]- | 208114-14-1 |
| 58 | 1-Propanaminium, 34[3[3-(2H-benzotriazol-2-yl)-5-(1,1-dimethylethyl]-4-hydroxyphenyl]-1-oxopropyl]amino]-N,N-diethyl-N-methyl-, methyl sulfate (salt) | 340964-15-0 |
| 59 | 2-Propenoic acid, 3-(1H-imidazol-4-yl)- | 104-98-3 |
| 60 | Benzoic acid, 2-hydroxy-, [4-(1-methylethyl)phenyl]methyl ester | 94134-93-7 |
| 61 | 1,2,3-Propanetriol, 1-(4-aminobenzoate); glyceryl PABA | 136-44-7 |
| 62 | Benzeneacetic acid, 3,4-dimethoxy-a-oxo- | 4732-70-1 |
| 63 | 2-Propenoic acid, 2-cyano-3,3-diphenyl-, ethyl ester | 5232-99-5 |
| 64 | Anthralinic acid, p-menth-3-yl ester | 134-09-8 |
| 65 | 2,2'-bis(1,4-phenylene)-1H-benzimidazole-4,6-disulphonic acid mono sodium salt or Disodium phenyl dibenzimidazole tetrasulfonate or Neoheliopan AP | 349580-12-7, |
| 66 | 1,3,5-Triazine-2,4,6-triamine, N,N1-bis[445-(1,1-dimethylpropyl)-2-benzoxazolyl]phenyl]-N''-(2-ethylhexyl)- or Uvasorb K2A | 288254-16-0 |
| 67 | Merocyanine derivatives as described in WO 2004006878 and in IPCOM000022279D | |

68

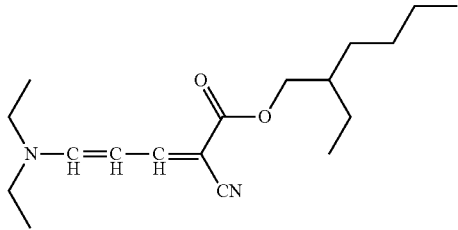 [SMILES: CCCCC(CC)COC(=O)C(C#N)=CC=CN(CC)CC]

68 sterols (cholesterol, lanosterol, phytosterols), as described in WO0341675
69 mycosporines and/or mycosporine-like amino acids as described in WO2002039974, e.g. Helioguard 365 from Milbelle AG, isolated mycosporine like amino acids from the red alga porphyra umbilicalis (INCI: Porphyra Umbilicalis) that are encapsulated into liposomes,)
70 alpha-lipoic-acid as described in DE 10229995
71 synthetic organic polymers as described in EP 1371358, [0033]-[0041]
72 phyllosilicates as described in EP 1371357 [0034]-[0037]
73 silica compounds as described in EP1371356, [0033]-[0041]
74 inorganic particles as described in DE10138496 [0043]-[0055]
75 latex particles as described in DE10138496 [0027]-[0040]

| 76 | 1H-Benzimidazole-4,6-disulfonic acid, 2,2'-(1,4-phenylene)bis-, disodium salt ; Bisimidazylate; Neo Heliopan APC | 180898-37-7 |
|---|---|---|

| Suitable UV filter substances which can be additionally used | |
|---|---|
| DE 100331804 | Tab 1 p 4, tab 2 + 3 p 5 |
| EP 613893 | Ex 1-5 + 15, T 1, pp 6-8 |
| EP 1000950 | Comp. in table 1, pp 18-21 |
| EP 1005855 | T 3, p 13 |
| EP 1008586 | Ex 1-3, pp 13-15 |
| EP 1008593 | Ex 1-8, pp 4-5 |
| EP 1027883 | Compound VII, p 3 |
| EP 1027883 | Comp I-VI, p 3 |
| EP 1028120 | Ex 1-5, pp 5-13 |
| EP 1059082 | Ex 1; T 1, pp 9-11 |
| EP 1060734 | T 1-3, pp 11-14 |
| EP 1064922 | Compounds 1-34, pp 6-14 |
| EP 1081140 | Ex 1-9, pp 11-16 |
| EP 1103549 | Compounds 1-76, pp 39-51 |
| EP 1108712 | 4,5-Dimorpholino-3-hydroxypyridazine |
| EP 1123934 | T 3, p 10 |
| EP 1129695 | Ex 1-7, pp 13-14 |
| EP 1167359 | Ex 1 p11 and ex 2 p 12 |
| EP 1258481 | Ex 1, pp 7,8 |
| EP 420707 B1 | Ex 3, p 13 (CAS Regno 80142-49-0) |
| EP 503338 | T 1, pp 9-10 |
| EP 517103 | Ex 3, 4, 9, 10 pp 6-7 |
| EP 517104 | Ex 1, T 1, pp 4-5; Ex 8, T 2, pp 6-8 |
| EP 626950 | all compounds |
| EP 669323 | Ex 1-3, p 5 |
| EP 780382 | Ex 1-11, pp 5-7 |
| EP 823418 | Ex 1-4, pp 7-8 |
| EP 826361 | T 1, pp 5-6 |
| EP 832641 | Ex 5 + 6 p 7; t 2, p 8 |
| EP 832642 | Ex 22, T 3 pp, 10-15; T 4, p 16 |
| EP 852137 | T 2, pp 41-46 |
| EP 858318 | T 1, p 6 |
| EP 863145 | Ex 1-11, pp 12-18 |

| Suitable UV filter substances which can be additionally used | |
|---|---|
| EP 895776 | Comp. in rows 48-58, p 3; R 25 + 33, p 5 |
| EP 911020 | T 2, p 11-12 |
| EP 916335 | T 2-4, pp 19-41 |
| EP 924246 | T 2, p 9 |
| EP 933376 | Ex 1-15, pp 10-21 |
| EP 944624 | Ex 1 + 2, pp13-15 |
| EP 945125 | T 3 a + b, pp 14-15 |
| EP 967200 | Ex 2; T 3-5, pp 17-20 |
| EP 969004 | Ex 5, T 1, pp 6-8 |
| JP 2000319629 | CAS Regno. 80142-49-0, 137215-83-9, 307947-82-6 |
| US 5635343 | all compounds on pp 5-10 |
| US 5338539 | Ex 1-9, pp 3 + 4 |
| US 5346691 | Ex 40, p 7; T 5, p 8 |
| US 5801244 | Ex 1-5, pp 6-7 |
| WO 0149686 | Ex 1-5, pp 16-21 |
| WO 0168047 | Tables on pp 85-96 |
| WO 0181297 | Ex 1-3 pp 9-11 |
| WO 0238537 | All componds p 3, compounds on rows 1-10 p 4 |
| WO 9217461 | Ex 1-22, pp 10-20 |
| WO 9220690 | Polymeric comp in examples 3-6 |
| WO 9301164 | T 1 + 2, pp 13-22 |
| WO 9714680 | Ex 1-3, p 10 |

(Abbreviations T: table, R: row, Comp: compound, Ex: compound(s) of patent example, p: page);
the generic scope of the UV absorbers is described in the left-hand column;
specific compounds are indicated in the right-hand column As water- and oil-containing emulsions (e.g. W/O, O/W, O/W/O and W/O/W emulsions or microemulsions) the preparations contain, for example, from 0.1 to 30% by weight, preferably from 0.1 to 15% by weight and especially from 0.5 to 10% by weight, based on the total weight of the composition, of one or more UV absorbers, from 1 to 60% by weight, especially from 5 to 50% by weight and preferably from 10 to 35% by weight, based on the total weight of the composition, of at least one oil component, from 0 to 30% by weight, especially from 1 to 30% by weight and preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically acceptable adjuvants.

Cosmetic or pharmaceutical preparations in general can be prepared by physically mixing the active component(s) with the adjuvant using customary methods, for example by simply stirring together the individual components.

Examples for compounds especially useful in the present invention include those listed below:

AO3: Reaction product of glycerine, coconut oil and a compound of the formula

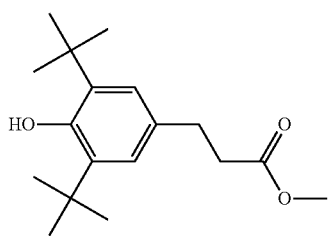

(mixture of mono-, di- and triglycerides of β-(3,5-di-tert.butyl-4-hydroxyphenyl) propanoic acid and fatty acids, CAS Reg.-No. 179986-09-5)

AO4:

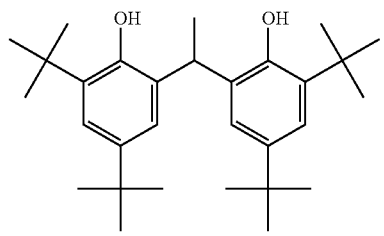 [SMILES: CC(c1cc(C(C)(C)C)cc(C(C)(C)C)c1O)c1cc(C(C)(C)C)cc(C(C)(C)C)c1O]

AO5 is a mixture of the compounds of the formulae:

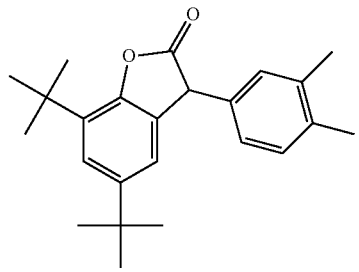

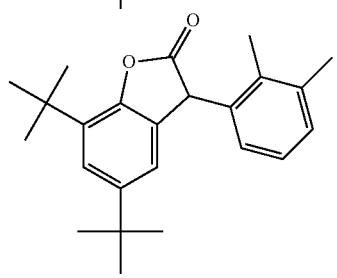

AO6:

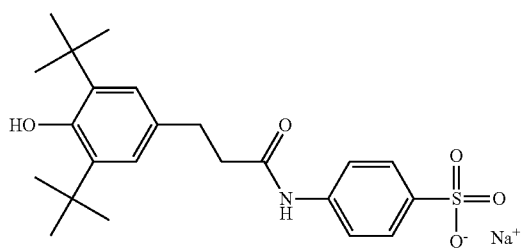 [SMILES: CC(C)(C)c1cc(CCC(=O)Nc2ccc(S(=O)(=O)[O-])cc2)cc(C(C)(C)C)c1O ; [Na+]]

AO7: pentaerythritol-tetrakis(3-[3',5'-di-tert.butyl-4'-hydroxyphenyl]-propionate)

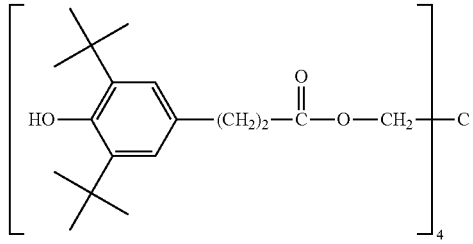

(CAS Reg.-No. 006683-19-8)

AO8:

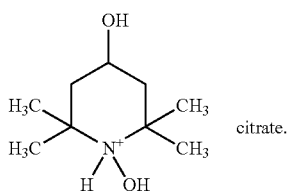

citrate.

The following Examples will serve to illustrate the invention without implying any restriction to what is described therein. Unless otherwise indicated, percentages are by weight.

ABBREVIATIONS

DMSO dimethylsulfoxide
EDTA ethylene-diamine tetraacetic acid
ELISA enzyme linked immunosorbent assay
FCS fetal calf serum

EXAMPLE 1

Cell Toxicity

Cell cultures: Primary human dermal fibroblasts (HDF-N2) are maintained in Dulbecco's culture media (DMEM; 1 g/l glucose), supplemented with 10% of fetal calf serum (FCS), 100 µg/ml of streptomycin sulphate, 100 µml of penicillin and 2 mM of L-glutamine, all of them from Biowhitaker, USA. Confluent cells are detached by incubation for 3 minutes in 0.055 trypsin/0.53 mM EDTA at 37° C. and plated at the established cell density (normally, $15 \times 10^4$ cells/cm$^2$).

Testing: Stock solutions of each test compound (active) in DMSO or in ethanol (5%) are diluted into the cell culture medium containing 10% FCS (see above) as indicated in table 1. Culture media of negative controls are containing 10 mMol NaCl or 0.05% DMSO or 0.05% ethanol, respectively. Positive control is a culture medium containing 0.02% of Sodium Lauryl Sulfate (SDS).

For comparative purposes, a further culture medium is used containing the compound of the formula

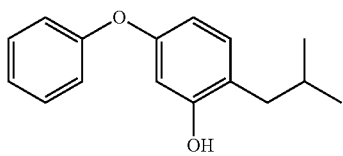

(comparison)

in the same dilution.

The test media thus obtained are added for 24 h to 48 h-cultures of Human Dermal Fibroblast (HDF) described above, and the rate of survival is measured via a specific color marker penetrating only into live-cells (The more absorption at OD$_{450}$, the more viable cells: Living dermal fibroblast possess an esterase that liberates a color, which absorbs at 450 nm. Dead cells do not. Measuring in cell cultures in presence of test substances the OD450 and comparing it to non-treated controls yields thus a measure for cell toxicity). Results are compiled in the following table.

TABLE 1

| Absorbance (OD$_{450}$) after 24 h treatment | |
|---|---|
| active | OD$_{450}$ |
| none (NaCl) | 2.2 |
| none (DMSO) | 2.1 |
| control (SDS) | 0.25 |
| AO3 1:500 | 1.55 |
| AO4 1:500 | 1.0 |
| AO5 1:500 | 1.45 |
| AO6 1:500 | 1.9 |
| AO7 1:500 | 2.0 |
| AO8 1:500 | 1.65 |
| comparison 1:500 | 0.25 |

Cytotoxicity of the present test compounds is in an acceptable range.

EXAMPLE 2

Anti-Inflammatory Activity (In Vitro)

Compounds are tested for anti-inflammatory activities via their capability of modifying the basal PGE$_2$ release in HDF-N2 cultivated as described in example 1.

For this purpose, cells are cultured in 24 well culture plates for 3 days. Before treatment confluent cells are arrested for 24 h with culture media containing 1% FCS and then treated for 18-24 h with selected concentrations of the test compounds. Each of the test compounds AO3, AO5, AO6 and AO7, respectively, is applied in dilutions 1:500, 1:1000 and 1:1500, each prepared by adding appropriate amounts of the stock solution described in example 1 to the culture medium.

After treatment, cells supernatants are removed and aliquots stored at −20° C. until analysis of PGE$_2$ using an ELISA kit from Amersham Biosciences. The PGE$_2$ values (pg/well) are individually corrected for the total protein, measured by the BCA Method (Pierce) and expressed as PGE$_2$ (pg/mg protein or ng/mg protein).

Morphological control of culture at 24 h of product application is performed by phase contrast microscopy.

Results: The test compounds show good PGE$_2$ inhibition activity.

EXAMPLE 3

Evaluation of the Efficacy of Present Compounds Against Photooxidative Stress in the Skin Induced by UVA Irradiation Anti-oxidant activity in vivo is measured via the capacity of a test compound to reduce radical induced lipid-peroxidation.

Persons tested: 10 individuals (4 female, 6 male); age range: 18 to 32 years
Body region tested: inner forearm
Application phase: once a day
Test period 7 days
Evaluation method: Determination of squalene
　　Determination of squalenehydroperoxide
Time of Evaluation: after UVA radiation
Evaluation: Descriptive statistics: average, median, minimum, maximum, variance, standard error, standard deviation; Multiple range test.

Test Method

Each test compound (active) is applied as a 1% b.w. solution in ethanol, except for AO7 where a 0.1% b.w. solution in ethanol is applied; in the following, these test solutions are also recalled as formulation. On the inner forearm of each subject symmetrically opposed areas are defined. The different formulations are applied once a day at a dose of about 2 mg of test solution/$cm^2$ for one week (application with a syringe for fine dosage: Omnifix®-F 1 ml; manufacturer: Braun Melsungen AG, Germany).

Two areas remain untreated.

The unique application of a solution of tocopherol in ethanol (0.2%) before irradiation serves as control.

Use of other cosmetic products is restricted on the test areas throughout the whole study. The areas (exception: one of the two untreated areas was not irradiated and can be attributed to environmental UVA radiation during the test) of the subject's back were then irradiated with UVA light (10 joule/$cm^2$). The lipids present on the test areas are harvested via a solvent extraction (4 ml ethanol for 2 minutes). The samples are first filtered through hydrophobic polypropylene filters to decant squames and other insoluble material, then dried under nitrogen at room temperature and taken up in 1 ml ethanol. Squalene (SQ) and squalenehydroperoxide (SQOOH) are then analysed by High Performance Liquid Chromatography (HPLC).

The results are expressed as the rate of inhibition relative to the untreated area:

% inhibition=100×[SQOOH(untreated)−SQOOH(active)]/SQOOH(untreated)

(SQOOH in pmoles hydrogen peroxide per pg squalene)

HPLC Analysis for SQ column: LiChrospher® 100 RP-18 (5 μm, 125×4 mm) Merck-Germany mobile phase:
acetonitrile/isopropanol (1/1; V/V)
detection: UV 210 nm
flow rate: 1 ml/min
injection volume: 20 μl
equipment: Beckman System Gold (USA) with Programmable Solvent Module 126 and Programmable Detector Module 166

HPLC Analysis for SQOOH column: LiChrospher® 100 RP-Select B (5 μm, 125×4 mm) Merck-Germany
mobile phase: methanol
detection: Chemiluminescence (post column detection)
flow rate: 1 ml/min
injection volume: 20 μl
reaction solution: Luminol (1 μg/ml) and Cytochrom C (10 μg/ml solved in 50 mM Borate-buffer, pH 10)
equipment: Beckman System Gold (USA) with Programmable Solvent Module 126 and fluorometer RF-551 (Shimadzu, Japan)

The fluorometer is used as a photon detector with the excitation source turned off.

This assay measures the hydroperoxy groups themselves and not indirect indices of lipid peroxidation such as conjugated dienes or breakdown products of lipid hydroperoxides. Chemiluminescence also detects ubiquinols. To confirm that any chemiluminescence observed in this assay was due to a hydroperoxide, not a hydroquinone, some samples were reduced with triphenyl phosphine and rerun. Since the chemiluminescence response of hydroperoxides, but not of hydroquinones, is eliminated by triphenyl phosphine, the disappearance of chemiluminescence peaks in the treated samples indicated that chemiluminescence observed in this assay was due to hydroperoxides and not hydroquinones.

Biometry

Measuring data are centrally computerised after validity check and quality assurance. Evaluation is done using the software Statgraphics for Windows, Version 5.0—Manugistics, USA. Data are analysed by multiple range test (LSD: Least Significant Differences). The 0.05 level is selected as the point of minimal acceptance statistical significance.

Results

The present skincare formulations significantly ($p<0.05$) reduce squalene peroxidation, compared to UV radiated non-treated control.

In the untreated, non-irradiated area the formation of ethanol extractable squalenehydroperoxide is not detected.

The average inhibition in % of peroxidation is:

| Formulation | Inhibition |
|---|---|
| AO4 | 28% |
| AO5 | 26.5% |
| AO6 | 28% |
| AO7 | 21.5% |
| AO8 | 21% |
| Control | 22.5% |

Conclusion:

Pretreatment of the epidermal surface before exposure to UVA irradiation with the formulations according to the present invention significantly reduces UV-induced sebum peroxidation. These studies provide compelling evidence for the free radical hypothesis of UVA light induced cutaneous pathology: Lipid peroxidation increased on irradiation, and the topical application with an antioxidant system protected from this damage.

EXAMPLE 3

Dermatological Formulations

General Preparation:

A clear homogenous prephase is obtained by mixing
(a) 5 to 20% by weight of a phospholipid (e.g. lecithin),
(b) 15 to 40% by weight of a coemulsifier (e.g. a polyethoxylated sorbitan fatty acid ester, polyethoxylated fatty alcohol, polyethoxylated fatty acid, polyethoxylated vitamin E derivative, polyethoxylated lanoline or lanoline derivative, polyethoxylated fatty acid glyceride or partial glyceride, polyethoxylated alkylphenol, sulfuric acid semiester of a polyethoxylated fatty alcohol or salt thereof, polyethoxylated fatty amine or amide, polyethoxylated carbon hydrate),
(c) 30 to 70% by weight of a lipophilic component consisting of a triglyceride, a compound of the invention such as AO3-AO8, and optionally a further active agent, where the weight ratio of active agent(s):triglyceride usually ranges from 1:5 to 5:1, and
(d) 3 to 30% by weight of an alcohol such as ethanol,
with the sum of percentages of the components (a), (b), (c) and (d) adding to 100%, and
adding the liquid obtained to a water phase. The water phase (e.g. 90 kg) is placed, with stirring (e.g. magnetic agitator), at 50° C. in a vessel. The liquid prephase (e.g. 10 kg) is added to the water phase with stirring (e.g. with a magnetic agitator). The formulation thus obtained may be further diluted or admixed.

Vitamin a Palmitate Cream

A dispersion is obtained by mixing a clear prephase containing:

| vitamin A palmitate (1.7 × 10⁶ IU/g) | 0.45% |
|---|---|
| compound AO7 | 0.45% |
| soybean lecithin | 1.73% |
| miglyol 812 | 3.00% |
| polysorbate 80 | 3.40% |
| ethanol | 1.42% |
| to a water phase: | |
| 10 mm phosphate buffer, pH 6 | ad 100.00% |

Final preparation contains:

| cetyl alcohol | 10.00% |
|---|---|
| hydrogenated groundnut oil | 20.00% |
| polysorbate 60 | 5.00% |
| propylene glycol | 20.00% |
| phenoxyethanol | 0.50% |
| dispersion shown above | 23.00% |
| aqua purificata | ad 100.00% |

Good results are also achieved when compound AO7 is replaced by AO3, AO4 or AO5.

Solcoseryl 0.5% Hydrogel

A dispersion is obtained by mixing a clear prephase containing:

| solcoseryl | 1.00% |
|---|---|
| compound AO7 | 1.00% |
| soybean lecithin | 1.73% |
| polysorbate 80 | 3.40% |
| miglyol 812 | 3.45% |
| ethanol | 1.42% |
| to a water phase: | |
| 10 mm phosphate buffer, pH 6 | ad 100.00% |

Final preparation contains:

| sodium carboxymethylcellulose 450 cP | 3.50% |
|---|---|
| dispersion shown above | 50.00% |
| aqua purificata | ad 100.00% |

The preparation is pleasantly cooling and has good antiphlogistic action.

Skin Protecting W/O Lotion

A dispersion is obtained by mixing a clear prephase containing:

| vitamin E acetate | 2.00% |
|---|---|
| compound AO3 | 1.00% |
| soybean lecithin | 0.49% |
| polysorbate 80 | 1.86% |
| miglyol 812 | 0.71% |
| ethanol | 0.63% |
| to a water phase: | |
| aqua purificata | ad 100.00% |

Final preparation contains:

| glycerol sorbitan fatty acid ester | 2.0% |
|---|---|
| polyethoxy fatty acid ester | 2.0% |
| isopropylisostearate | 5.0% |
| mineral oil | 7.0% |
| isopropylpalmitate | 4.0% |
| wheat germ oil | 3.0% |
| propylene glycol | 3.8% |
| dispersion shown above | 5.0% |
| MgSO₄ × 7H2O | 0.7% |
| perfume | 0.5% |
| perservative, water | |

Good results are also achieved when compound AO3 is replaced by AO7, AO6 or AO8.

Day Cream with UV Protection (O/W)

A dispersion is obtained by mixing a clear prephase containing:

| parsol MCX | 2.59% |
|---|---|
| (octyl methoxycinnamate) | |
| Parsol 5000 | 1.11% |
| (4-methylbenzylidene camphor) | |
| compound AO7 | 1.00% |
| miglyol 812 | 1.30% |
| soybean lecithin | 0.50% |
| polysorbate 80 | 3.40% |
| ethanol | 1.10% |
| to a water phase: | |
| aqua purificata | ad 100.00% |

Final preparation contains:

| PEG-5 glycerol stearate | 5.0% |
|---|---|
| steareth-21 | 2.0% |
| mineral oil | 30.0% |
| cetyl alcohol | 2.0% |
| microcrystalline wax | 1.0% |
| propylene glycol | 6.0% |
| dispersion shown above | 10.0% |
| phenoxyethanol + methyl-, ethyl-, propyl-, butylparabene | 0.3% |
| water | ad 100.0% |

The invention claimed is:

1. A method for the local treatment or prevention of inflammatory conditions comprising:

administering to a patient in need of such treatment an effective amount of a pharmaceutical composition comprising at least one of the following compounds of formulae (7) to (35)

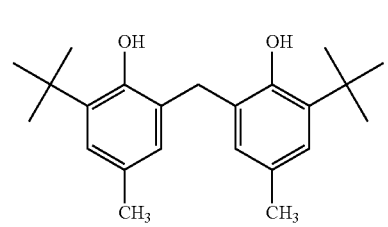

(7)

(8)
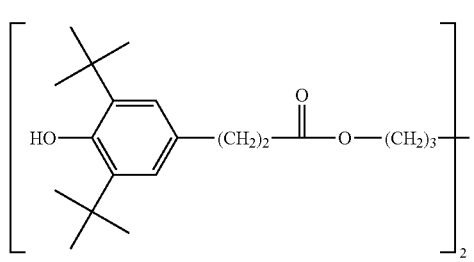
(9)
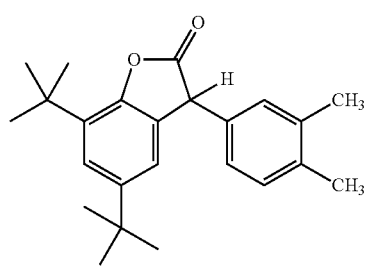
(10)
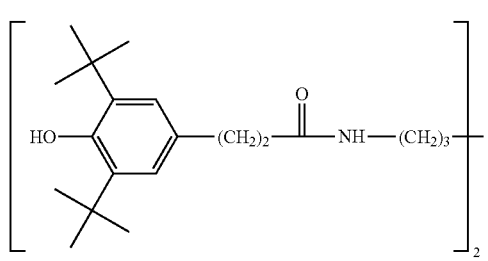
(11)
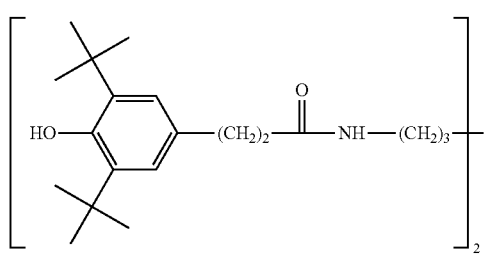
(12)
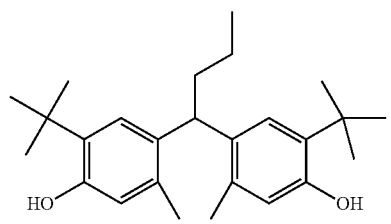
(13)
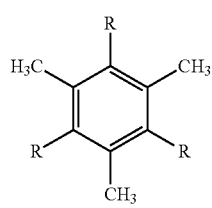
(14)
R = —CH$_2$— 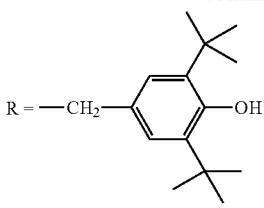
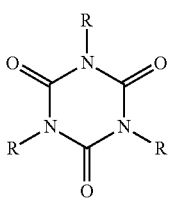
R = 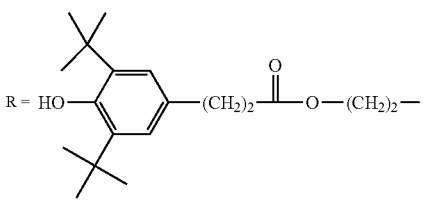
(15)
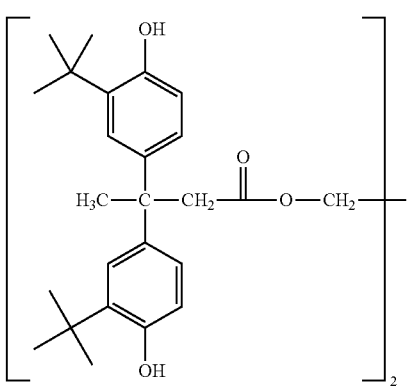
(16)
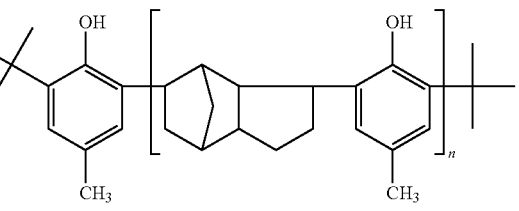
n = 1-3
(17)
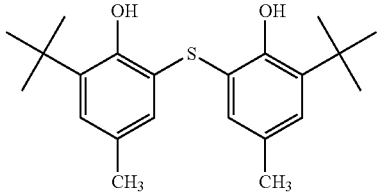

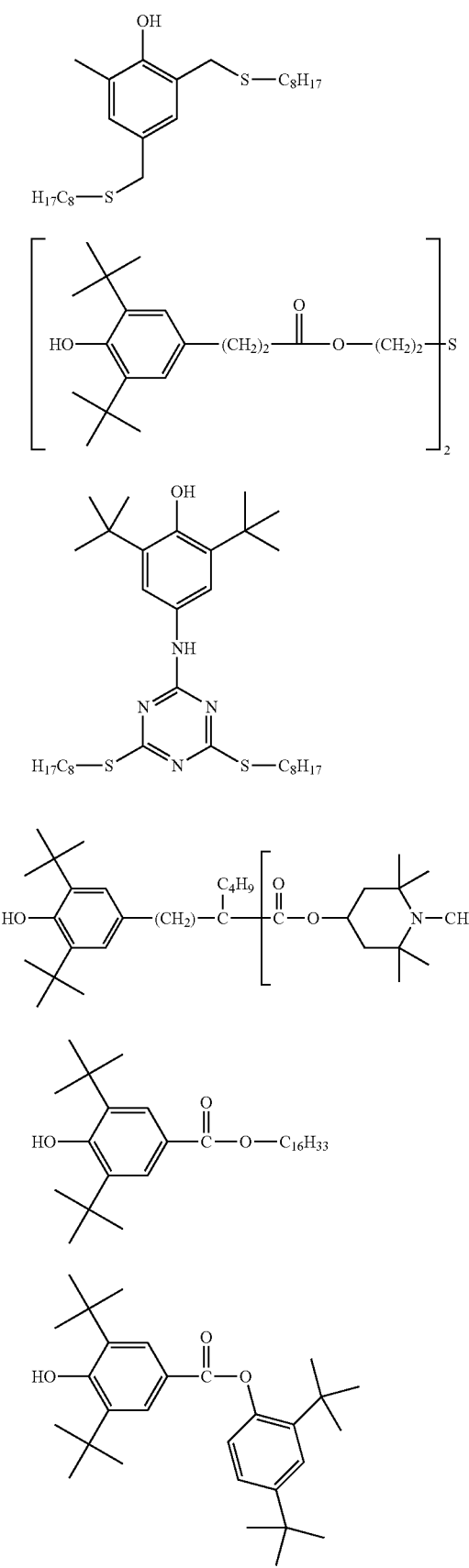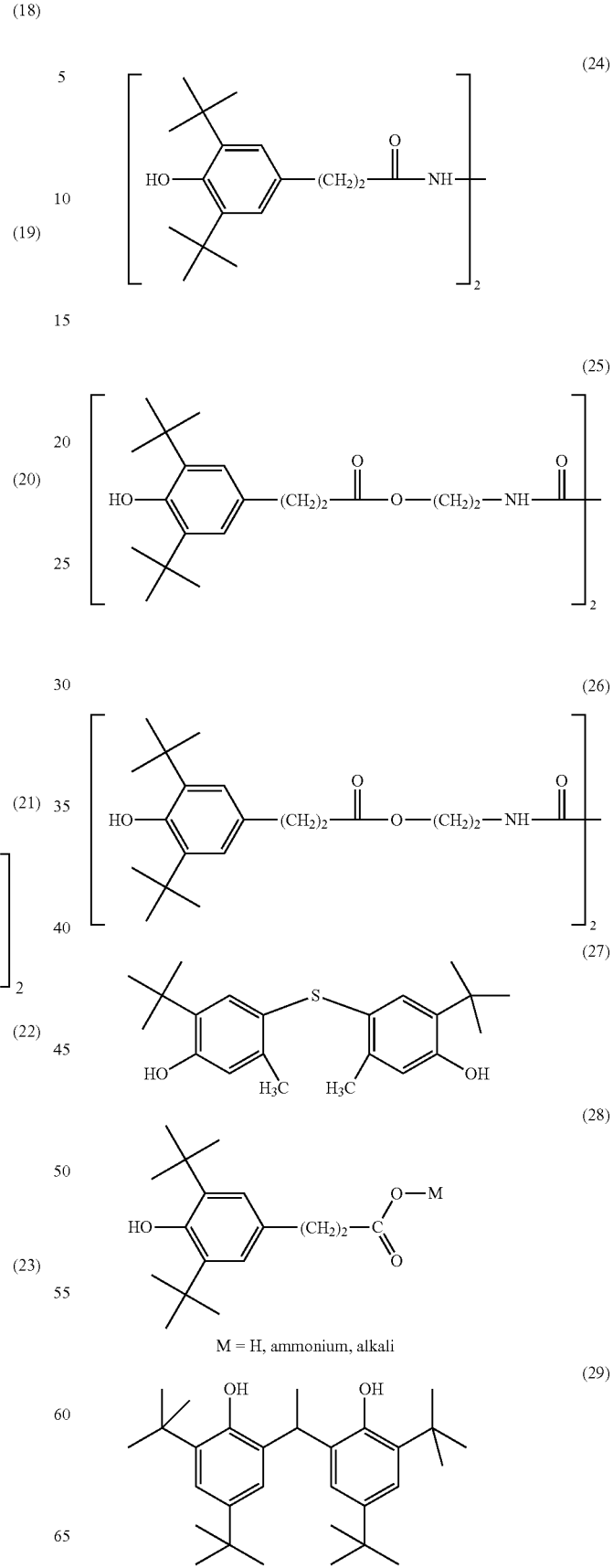

(30)

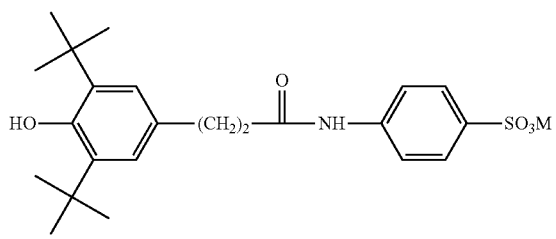

M = H, Na (31)

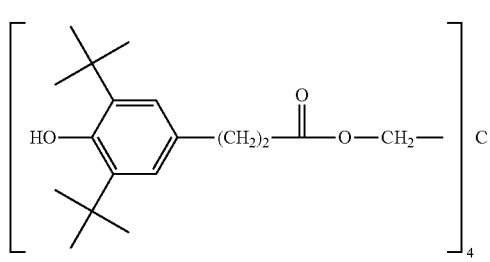

(32)

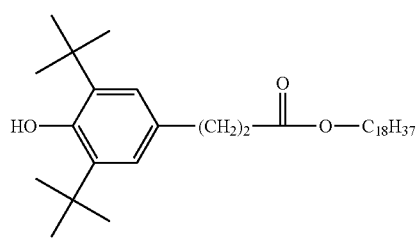

(33)

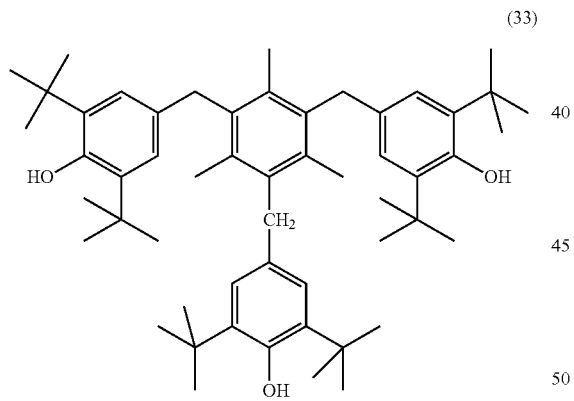

the reaction product of glycerine, coconut oil and a compound of the formula (34)

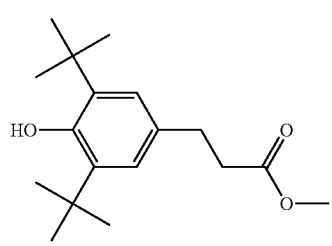

(35)

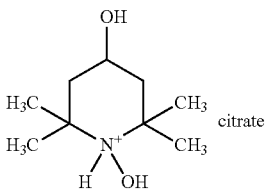

together with a pharmaceutically acceptable carrier or adjuvant, wherein the pharmaceutical composition is free from skin-lightening agents.

2. The method according to claim 1, wherein the compounds (7) to (35) are present in a total amount of 0.001 to 10% by weight of the total composition.

3. The method according to claim 1, which additionally comprises at least one substance selected from antiphlogistic agents, antiinflammatory agents, vitamins, antipsoriatic agents, further skin actives, cell proliferation regulators, antiallergic, UV protecting, moisturizing, antiageing agents, DNA-protectants.

4. The method according to claim 1, which contains the compounds (7) to (35), and optionally a further active ingredient, in nanodispersed or encapsulated form.

5. The method according to claim 1, wherein the following compounds are administered to a patient in need are selected from the group consisting of

AO3:

a reaction product of glycerine, coconut oil and a compound of the formula

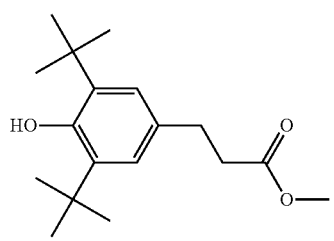

(mixture of mono-, di- and triglycerides of β-(3,5-di-tert.butyl-4-hydroxyphenyl) propanoic acid and fatty acids, CAS Reg.-No. 179986-09-5)

AO5 a mixture of the compounds of the formulae:

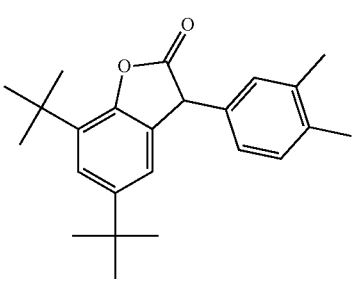

-continued

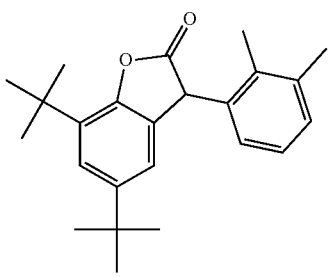

AO6:

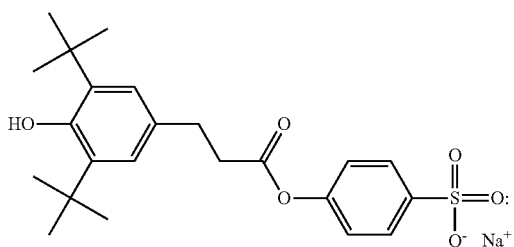

and

AO7: a pentaerythritol-tetrakis(3-[3',5'-di-tert.butyl-4'-hydroxyphenyl]-propionate)

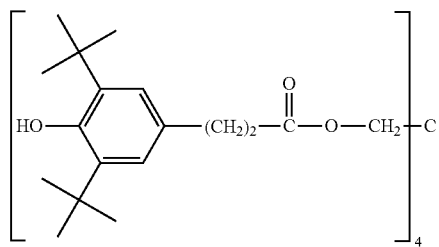

(CAS Reg. -No. 006683-19-8).

6. The method according to claim 1, wherein the compounds administered to the patient in need is selected from the group consisting of

AO3:

a reaction product of glycerine, coconut oil and a compound of the formula

AO5

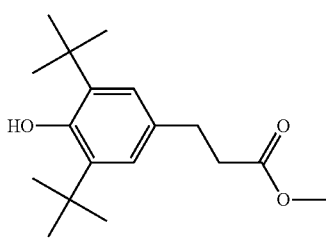 [SMILES: COC(=O)CCc1cc(C(C)(C)C)c(O)c(C(C)(C)C)c1]

a mixture of the compounds of the formulae:

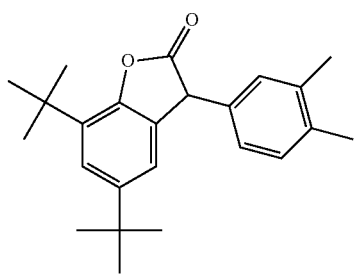

AO6:

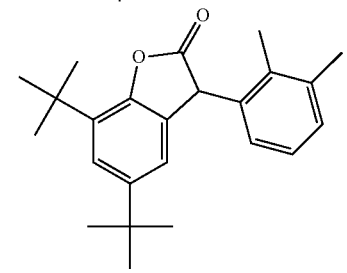

AO7: a pentaerythritol-tetrakis(3-[3',5'-di-tert.butyl-4'-hydroxyphenyl]-propionate)

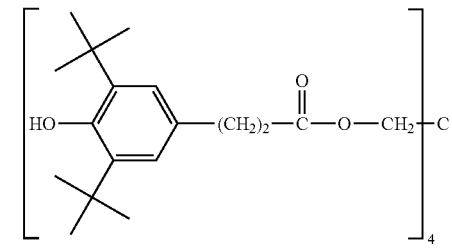

(CAS Reg. -No. 006683-19-8)

AO8:

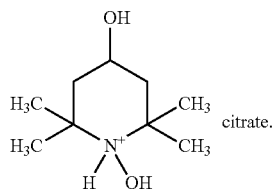

citrate.

7. The method according to claim 1, comprising administering the pharmaceutical composition to the patient in need of local treatment or prevention of inflammatory conditions for other than an after-sun inflammatory condition.

8. The method according to claim 1, wherein the inflammatory condition is an adverse radical induced inflammatory condition selected from the group consisting of collagen damage inflammation, reperfusion damage inflammation, DNA-damage inflammation, and combinations thereof.

9. The method according to claim 1, wherein the inflammatory condition is an adverse radical induced inflammatory condition selected from the group consisting of reperfusion damage inflammation, DNA-damage inflammation, and combinations thereof.

* * * * *